(12) United States Patent
Cabiri et al.

(10) Patent No.: US 8,523,881 B2
(45) Date of Patent: Sep. 3, 2013

(54) MULTIPLE ANCHOR DELIVERY TOOL

(75) Inventors: Oz Cabiri, Macabim-Reut (IL); Amir Gross, Tel-Aviv (IL); Tal Hammer, Ramat Gan (IL); Tal Reich, Binyamina (IL); Ehud Iflah, Tel Aviv (IL)

(73) Assignee: Valtech Cardio, Ltd., Or Yehuda (IL)

( * ) Notice: Subject to any disclaimer, the term of this patent is extended or adjusted under 35 U.S.C. 154(b) by 202 days.

(21) Appl. No.: 12/843,412

(22) Filed: Jul. 26, 2010

(65) Prior Publication Data

US 2012/0022557 A1  Jan. 26, 2012

(51) Int. Cl.
*A61B 17/10* (2006.01)

(52) U.S. Cl.
USPC .......................................... 606/139; 623/349

(58) Field of Classification Search
USPC ................. 606/139, 142, 143, 213, 305, 308; 411/16, 347, 349, 402, 407
See application file for complete search history.

(56) References Cited

U.S. PATENT DOCUMENTS

| | | |
|---|---|---|
| 4,602,911 A | 7/1986 | Ahmadi et al. |
| 4,917,698 A | 4/1990 | Carpenter et al. |
| 5,061,277 A | 10/1991 | Carpentier et al. |
| 5,104,407 A | 4/1992 | Lam et al. |
| 5,258,008 A | 11/1993 | Wilk |
| 5,306,296 A | 4/1994 | Wright et al. |
| 5,477,856 A | 12/1995 | Lundquist |
| 5,669,919 A | 9/1997 | Sanders et al. |
| 5,674,279 A | 10/1997 | Wright et al. |
| 5,728,116 A | 3/1998 | Rosenman |
| 5,810,882 A * | 9/1998 | Bolduc et al. ................ 606/213 |
| 5,876,373 A | 3/1999 | Giba et al. |
| 5,961,440 A | 10/1999 | Schweich et al. |
| 5,961,539 A | 10/1999 | Northrup, III et al. |
| 6,045,497 A | 4/2000 | Schweich et al. |
| 6,050,936 A | 4/2000 | Schweich et al. |
| 6,059,715 A | 5/2000 | Schweich et al. |
| 6,165,119 A | 12/2000 | Schweich et al. |
| 6,251,092 B1 | 6/2001 | Qin et al. |

(Continued)

FOREIGN PATENT DOCUMENTS

| | | |
|---|---|---|
| WO | WO 01/26586 | 4/2001 |
| WO | WO 02/085251 | 10/2002 |

(Continued)

OTHER PUBLICATIONS

An Office Action dated Mar. 9, 2012, which issued during the prosecution of U.S. Appl. No. 12/689,635.

(Continued)

*Primary Examiner* — Corrine M McDermott
*Assistant Examiner* — Robert A Lynch
(74) *Attorney, Agent, or Firm* — Sughrue Mion, PLLC

(57) ABSTRACT

An anchor deployment tool includes a flexible outer tube, within which is positioned a flexible inner shaft, and a rotating deployment element coupled to a distal end of the shaft. The tool is configured to provide an anchor storage area, which initially stores a plurality of tissue anchors, such that the inner shaft passes through channels of the anchors along entire longitudinal lengths of the anchors, and the anchors are within the outer tube. The rotating deployment element is configured to directly engage the anchors in the anchor storage area one at a time, advance each of the anchors while engaged in a distal direction, and deploy each of the anchors through the distal tube end and into tissue of a subject. Other embodiments are also described.

24 Claims, 15 Drawing Sheets

(56) References Cited

U.S. PATENT DOCUMENTS

| | | | |
|---|---|---|---|
| 6,296,656 B1 | 10/2001 | Bolduc et al. |
| 6,319,281 B1 | 11/2001 | Patel |
| 6,332,893 B1 | 12/2001 | Mortier et al. |
| 6,402,780 B2 | 6/2002 | Williamson et al. |
| 6,406,420 B1 | 6/2002 | McCarthy et al. |
| 6,451,054 B1 | 9/2002 | Stevens |
| 6,524,338 B1 | 2/2003 | Gundry |
| 6,537,314 B2 | 3/2003 | Langberg et al. |
| 6,564,805 B2 | 5/2003 | Garrison et al. |
| 6,569,198 B1 | 5/2003 | Wilson et al. |
| 6,589,160 B2 | 7/2003 | Schweich et al. |
| 6,602,288 B1 | 8/2003 | Cosgrove |
| 6,602,289 B1 | 8/2003 | Colvin et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,651,671 B1 | 11/2003 | Donlon et al. |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,718,985 B2 | 4/2004 | Hlavka et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,786,924 B2 | 9/2004 | Ryan et al. |
| 6,802,319 B2 | 10/2004 | Stevens et al. |
| 6,805,710 B2 | 10/2004 | Bolling et al. |
| 6,858,039 B2 | 2/2005 | McCarthy |
| 6,893,459 B1 | 5/2005 | Macoviak |
| 6,908,482 B2 | 6/2005 | McCarthy et al. |
| 6,960,217 B2 | 11/2005 | Bolduc |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,087,064 B1 | 8/2006 | Hyde |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,229,452 B2 | 6/2007 | Kayan |
| 7,238,191 B2 | 7/2007 | Bachmann |
| 7,294,148 B2 | 11/2007 | McCarthy |
| 7,297,150 B2 | 11/2007 | Cartledge et al. |
| 7,311,728 B2 | 12/2007 | Solem et al. |
| 7,329,280 B2 | 2/2008 | Bolling et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,686,822 B2 | 3/2010 | Shayani |
| 8,070,804 B2 | 12/2011 | Hyde |
| 2001/0044656 A1* | 11/2001 | Williamson et al. ......... 623/2.11 |
| 2002/0087048 A1 | 7/2002 | Brock et al. |
| 2002/0103532 A1 | 8/2002 | Langberg et al. |
| 2002/0173841 A1 | 11/2002 | Ortiz et al. |
| 2003/0050693 A1 | 3/2003 | Quijano et al. |
| 2003/0105519 A1 | 6/2003 | Fasol et al. |
| 2003/0167062 A1 | 9/2003 | Gambale et al. |
| 2003/0233142 A1 | 12/2003 | Morales et al. |
| 2004/0024451 A1 | 2/2004 | Johnson et al. |
| 2004/0049207 A1 | 3/2004 | Goldfarb et al. |
| 2004/0092962 A1 | 5/2004 | Thornton et al. |
| 2004/0122514 A1 | 6/2004 | Fogarty et al. |
| 2004/0148021 A1 | 7/2004 | Cartledge et al. |
| 2004/0236419 A1 | 11/2004 | Milo |
| 2005/0004668 A1 | 1/2005 | Aklog et al. |
| 2005/0055087 A1 | 3/2005 | Starksen |
| 2005/0060030 A1 | 3/2005 | Lashinski et al. |
| 2005/0090827 A1 | 4/2005 | Gedebou |
| 2005/0171601 A1 | 8/2005 | Cosgrove et al. |
| 2005/0203549 A1 | 9/2005 | Realyvasquez |
| 2005/0267478 A1 | 12/2005 | Corradi et al. |
| 2005/0288781 A1 | 12/2005 | Moaddeb et al. |
| 2006/0020326 A9 | 1/2006 | Bolduc et al. |
| 2006/0025787 A1 | 2/2006 | Morales et al. |
| 2006/0041319 A1 | 2/2006 | Taylor et al. |
| 2006/0069429 A1 | 3/2006 | Spence et al. |
| 2006/0241656 A1 | 10/2006 | Starksen et al. |
| 2006/0241748 A1 | 10/2006 | Lee et al. |
| 2007/0016287 A1 | 1/2007 | Cartledge et al. |
| 2007/0027536 A1 | 2/2007 | Mihaljevic et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0112422 A1 | 5/2007 | Dehdashtian |
| 2007/0118151 A1 | 5/2007 | Davidson |
| 2007/0162111 A1 | 7/2007 | Fukamachi et al. |
| 2007/0213582 A1 | 9/2007 | Zollinger et al. |
| 2007/0219558 A1 | 9/2007 | Deutsch |
| 2007/0255400 A1 | 11/2007 | Parravicini et al. |
| 2007/0282375 A1 | 12/2007 | Hindrichs et al. |
| 2008/0004697 A1 | 1/2008 | Lichtenstein et al. |
| 2008/0058595 A1 | 3/2008 | Snoke et al. |
| 2008/0086203 A1 | 4/2008 | Roberts |
| 2008/0097523 A1 | 4/2008 | Bolduc et al. |
| 2008/0262609 A1 | 10/2008 | Gross et al. |
| 2009/0043153 A1 | 2/2009 | Zollinger et al. |
| 2009/0054969 A1 | 2/2009 | Salahieh et al. |
| 2009/0177266 A1 | 7/2009 | Powell et al. |
| 2010/0001038 A1* | 1/2010 | Levin et al. ................. 227/179.1 |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0286767 A1 | 11/2010 | Zipory et al. |
| 2011/0106247 A1 | 5/2011 | Miller et al. |

FOREIGN PATENT DOCUMENTS

| | | |
|---|---|---|
| WO | WO 02/085252 | 10/2002 |
| WO | WO 2006/097931 | 9/2006 |
| WO | WO 2006/116558 | 11/2006 |
| WO | WO 2007/136783 | 11/2007 |
| WO | WO 2008/068756 | 6/2008 |
| WO | WO 2010/004546 | 1/2010 |
| WO | WO 2010/073246 | 7/2010 |
| WO | 2010/128503 A2 | 11/2010 |
| WO | WO 2010/128502 | 11/2010 |
| WO | WO 2010/128503 | 11/2010 |

OTHER PUBLICATIONS

An International Search Report and a Written Opinion both dated Feb. 2, 2012, which issued during the prosecution of Applicant's PCT/IL11/00600.

O'Reilly S et al., "Heart valve surgery pushes the envelope," Medtech Insight 8(3): 73, 99-108 (2006).

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Swain CP et al., "An endoscopically deliverable tissue-transfixing device for securing biosensors in the gastrointestinal tract," Gastrointestinal Endoscopy 40(6): 730-734 (1994).

Odell JA et al., "Early Results of a Simplified Method of Mitral Valve Annuloplasty," Circulation 92:150-154 (1995).

An International Search Report dated Sep. 8, 2009, which issued during the prosecution of Applicant's PCT/IL09/000593.

U.S. Appl. No. 60/873,075, filed Dec. 5, 2006.

U.S. Appl. No. 60/902,146, filed Feb. 16, 2007.

U.S. Appl. No. 61/001,013, filed Oct. 29, 2007.

U.S. Appl. No. 61/132,295, filed Jun. 16, 2008.

"Two dimensional real-time ultrasonic imaging of the heart and great vessels", Mayo Clin Proc. vol. 53:271-303, 1978.

An International Search Report dated Jun. 10, 2010, which issued during the prosecution of Applicant's PCT/IL09/01209.

An Office Action dated Apr. 6, 2010, which issued during the prosecution of Applicant's U.S. Appl. No. 12/484,512.

An International Search Report and a Written Opinion, both dated Aug. 17, 2010, which issued during the prosecution of Applicant's PCT/IL10/00357.

An International Search Report and a Written Opinion, both dated Nov. 8, 2010, issued during the prosecution of Applicant's PCT/IL10/00358.

An International Preliminary Examination Report dated Dec. 29, 2010, which issued during the prosecution of Applicant's PCT/IL09/000593.

An Office Action dated Aug. 4, 2010, which issued during the prosecution of Applicant's U.S. Appl. No. 12/341,960.

An Office Action dated Oct. 6, 2010, which issued during the prosecution of Applicant's U.S. Appl. No. 12/484,512.

U.S. Appl. No. 61/207,908, filed Feb. 17, 2009.

U.S. Appl. No. 61/265,936, filed Dec. 2, 2009.

Brennan, Jennifer, "510(k) Summary of Safety and Effectiveness," Jan. 2008.

U.S. Appl. No. 12/608,316, filed Oct. 29, 2009.

U.S. Appl. No. 12/689,635, filed Jan. 19, 2010.

U.S. Appl. No. 12/689,693, filed Jan. 19, 2010.

U.S. Appl. No. 12/706,868, filed Feb. 17, 2010.

U.S. Appl. No. 12/785,717, filed May 24, 2010.

* cited by examiner

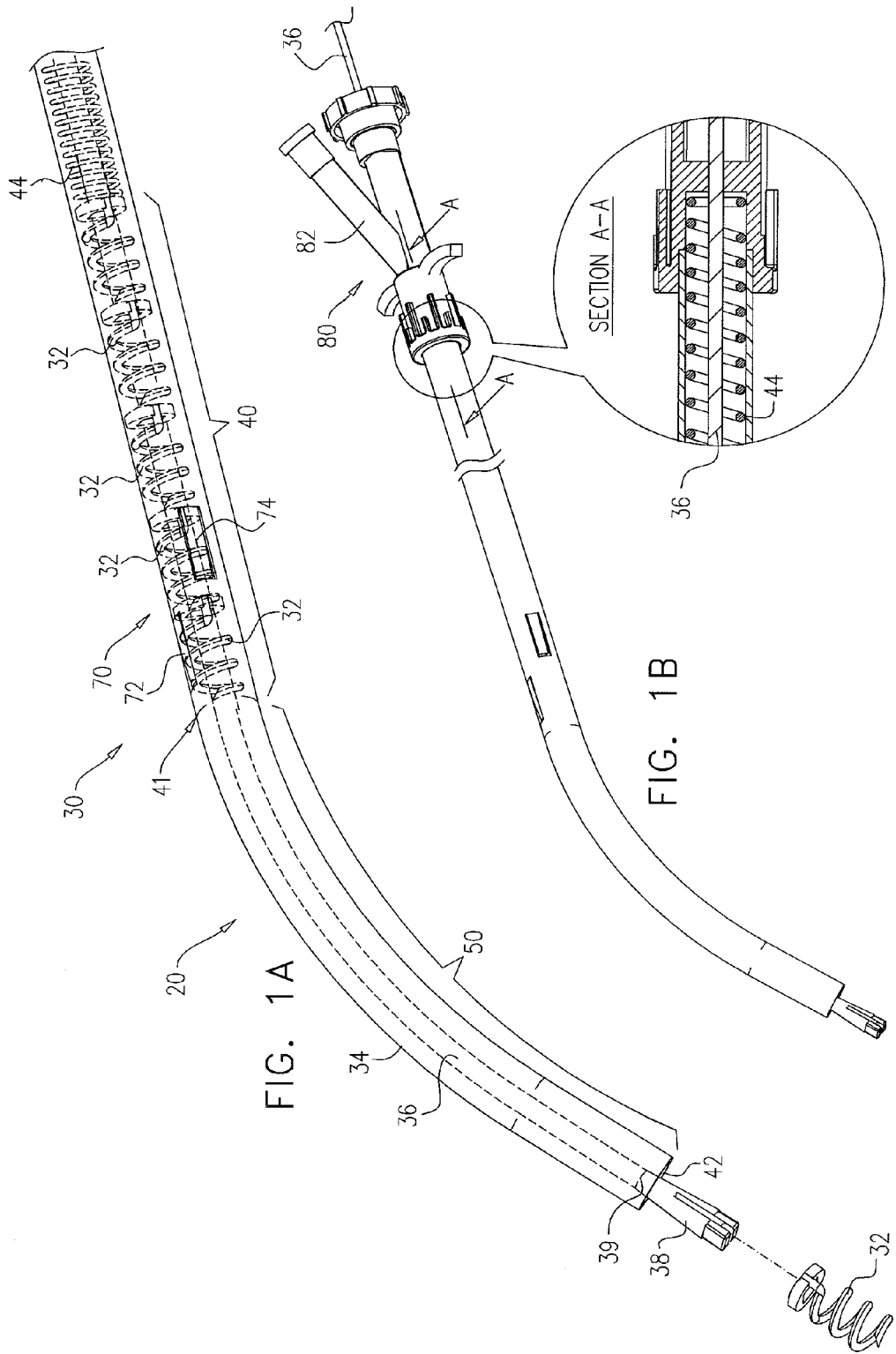

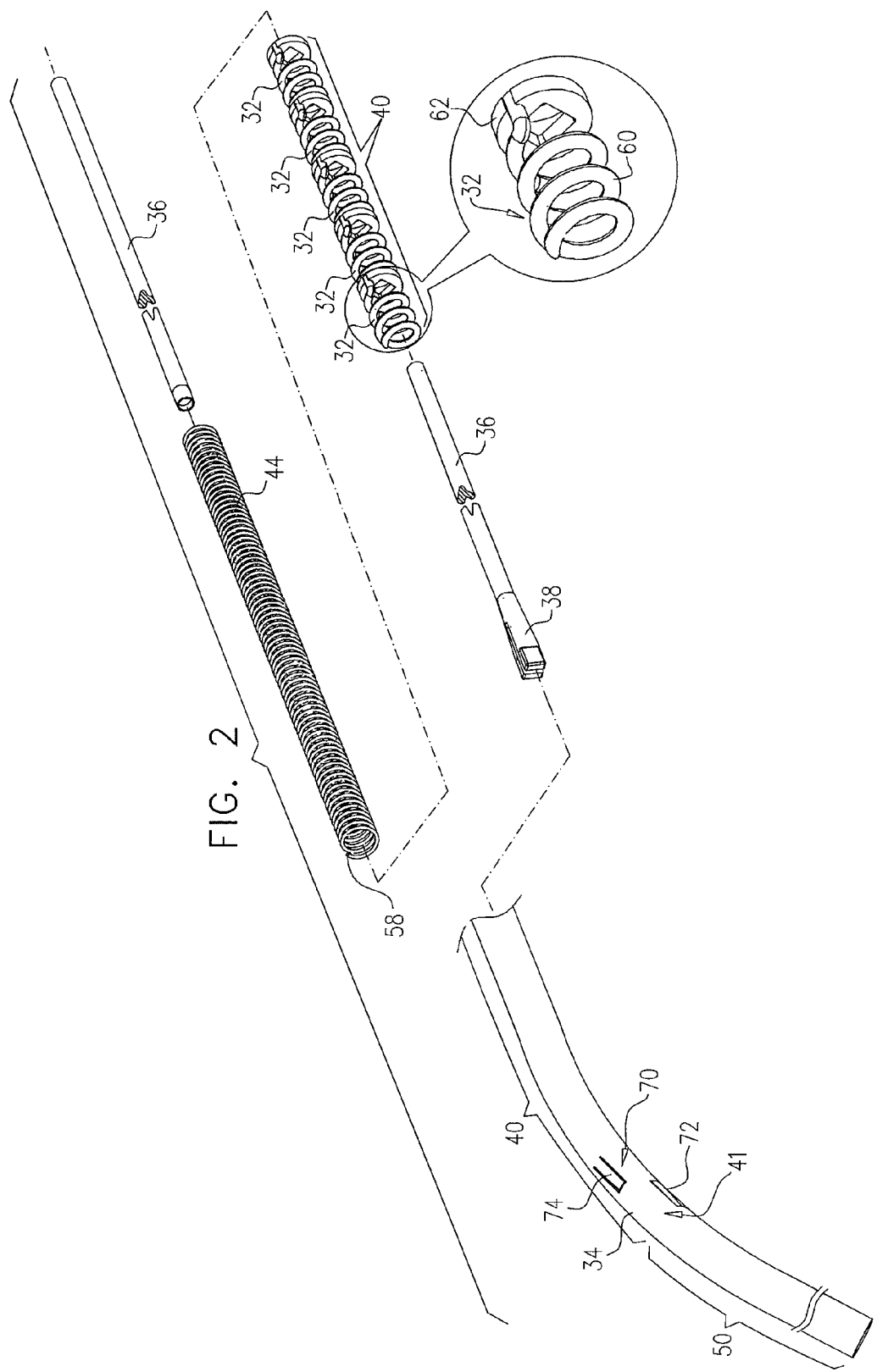

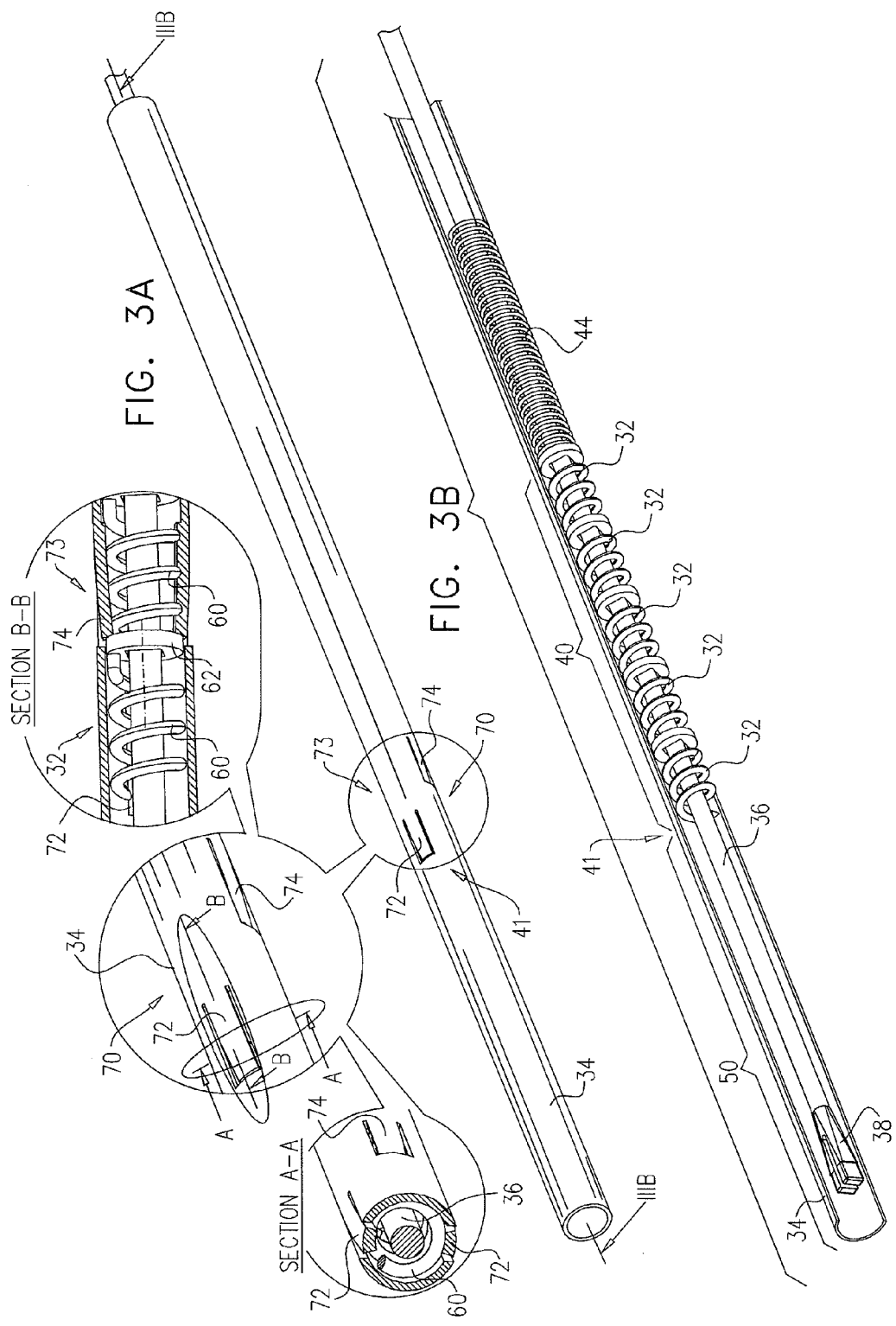

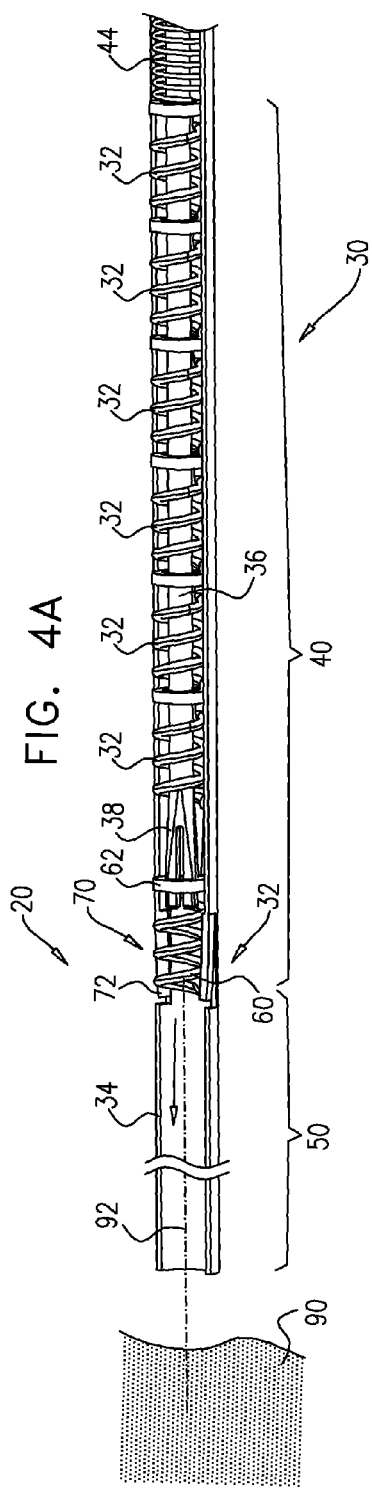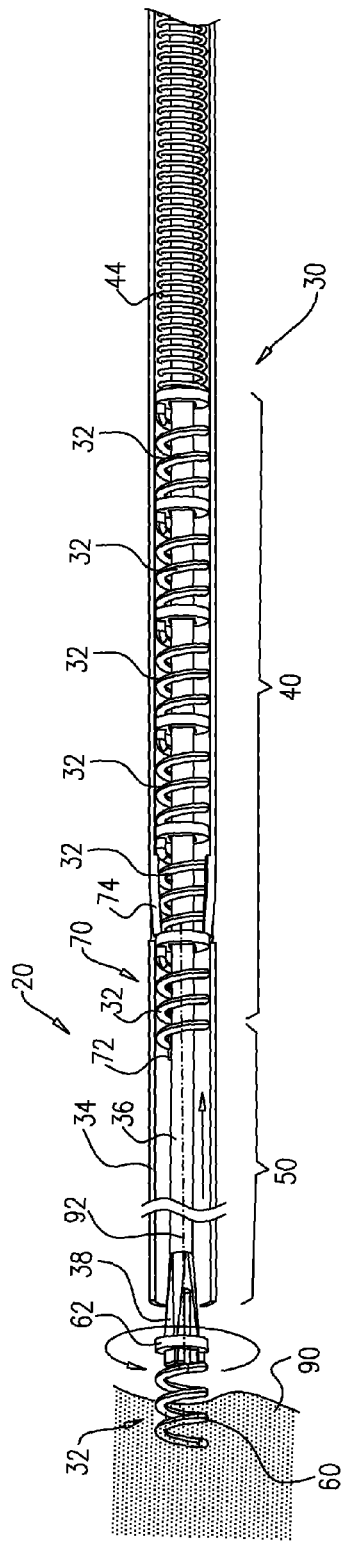

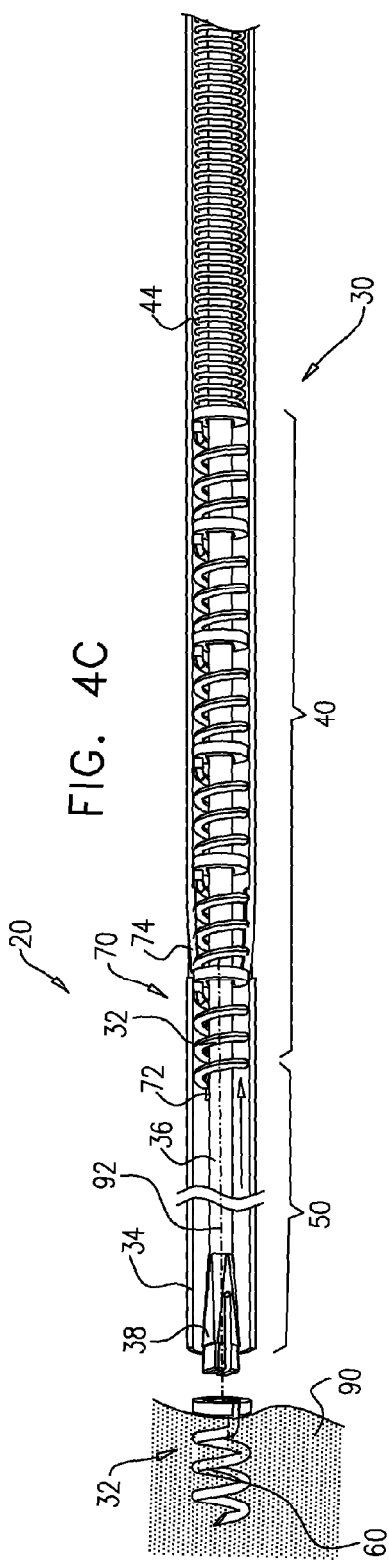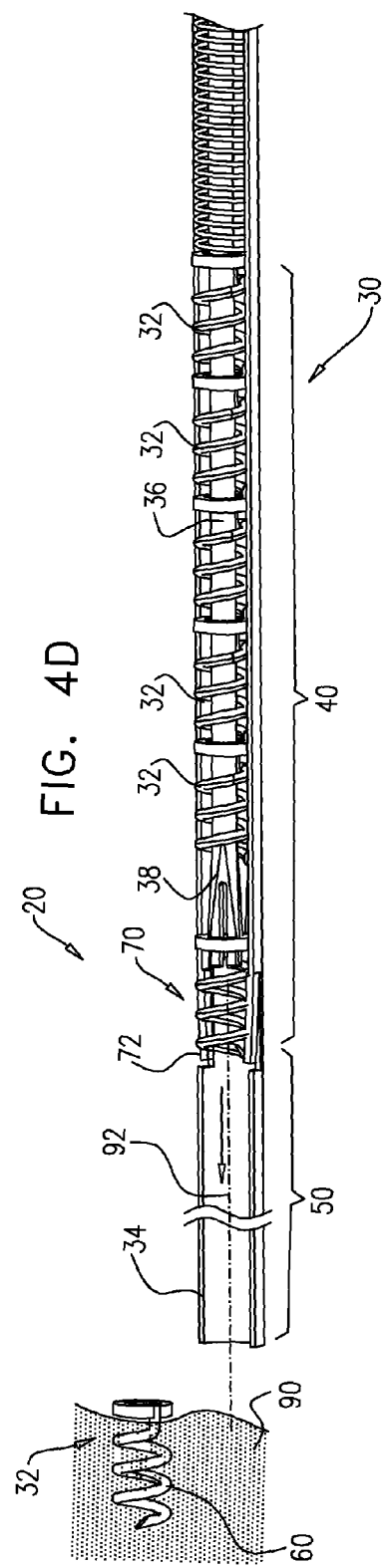

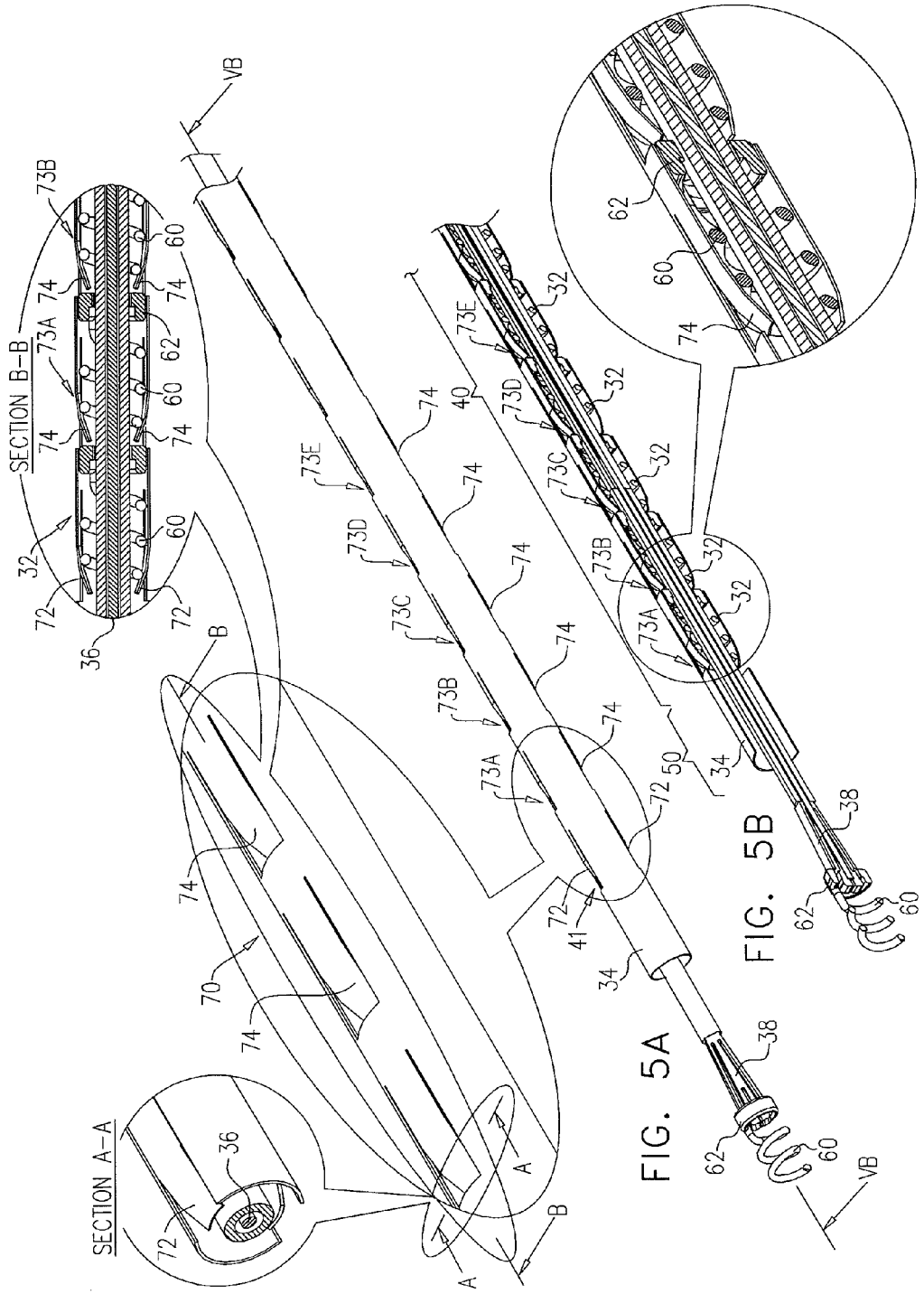

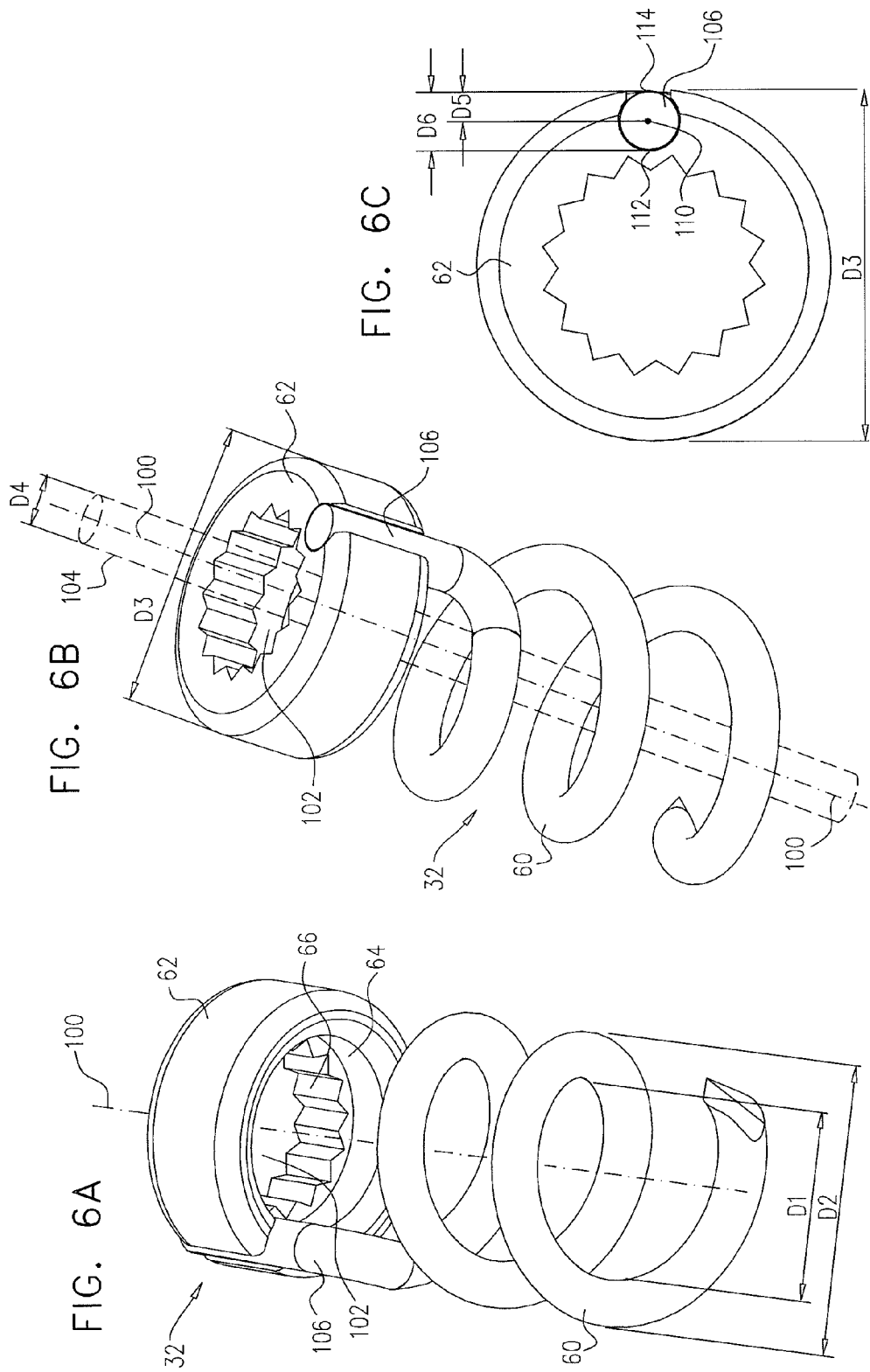

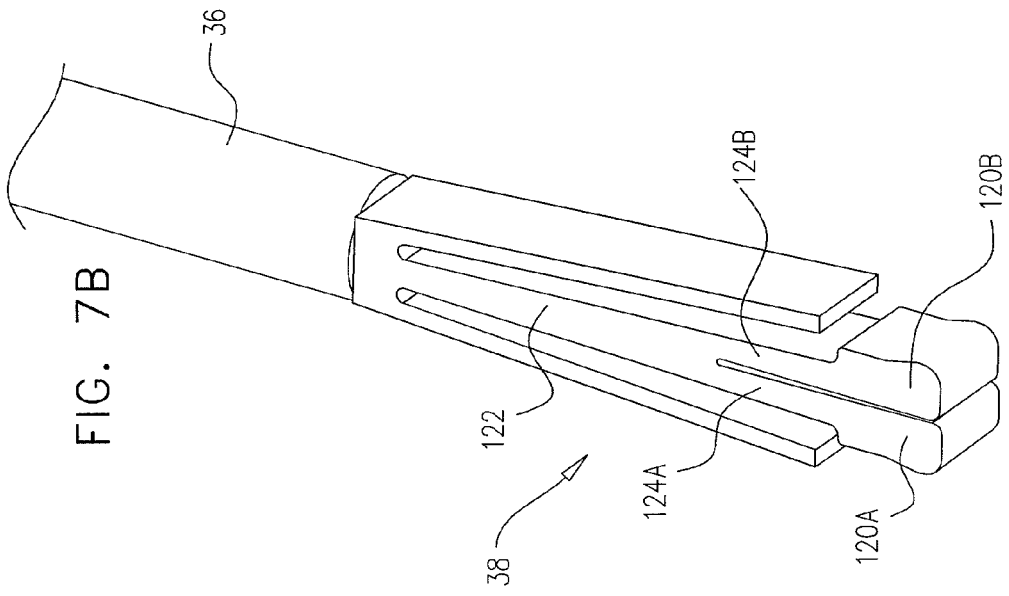
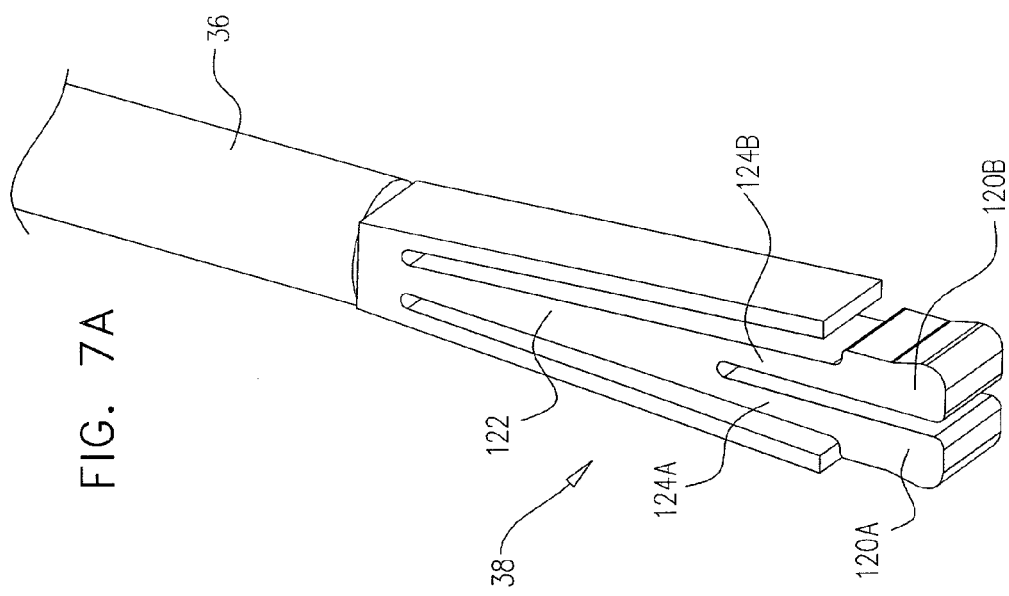

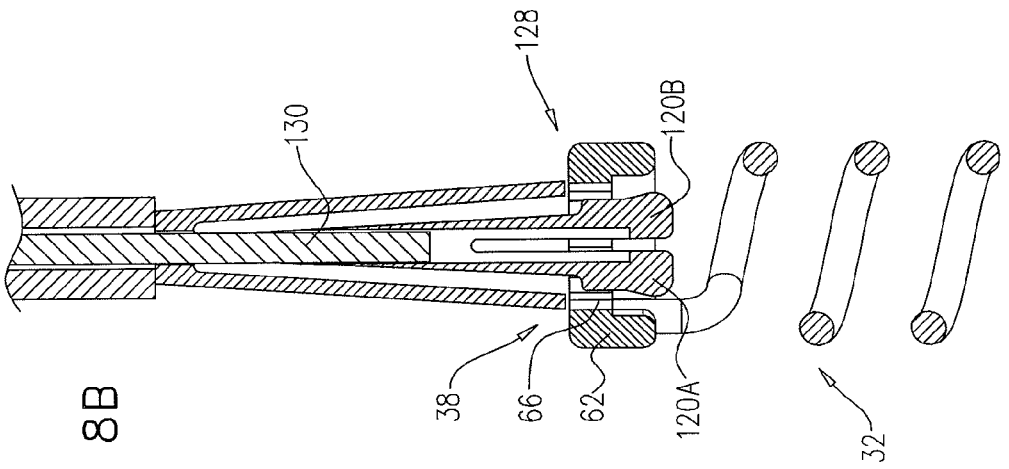
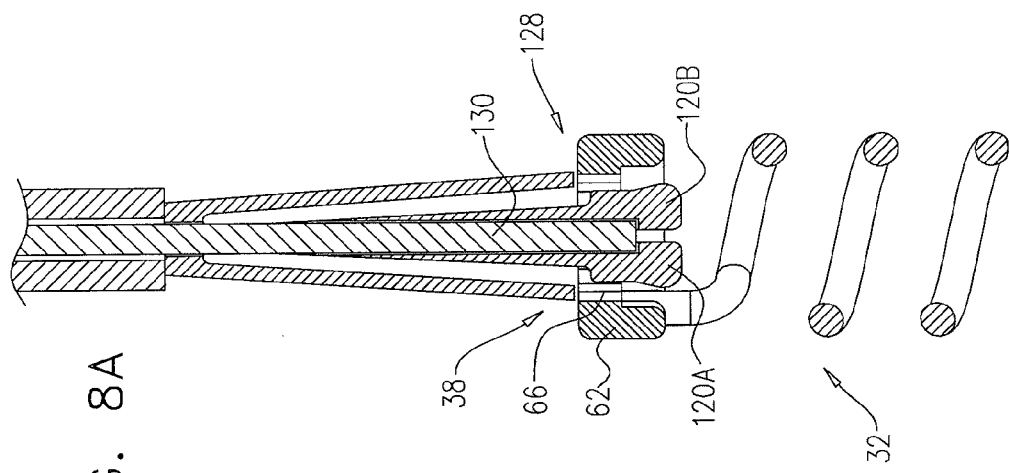

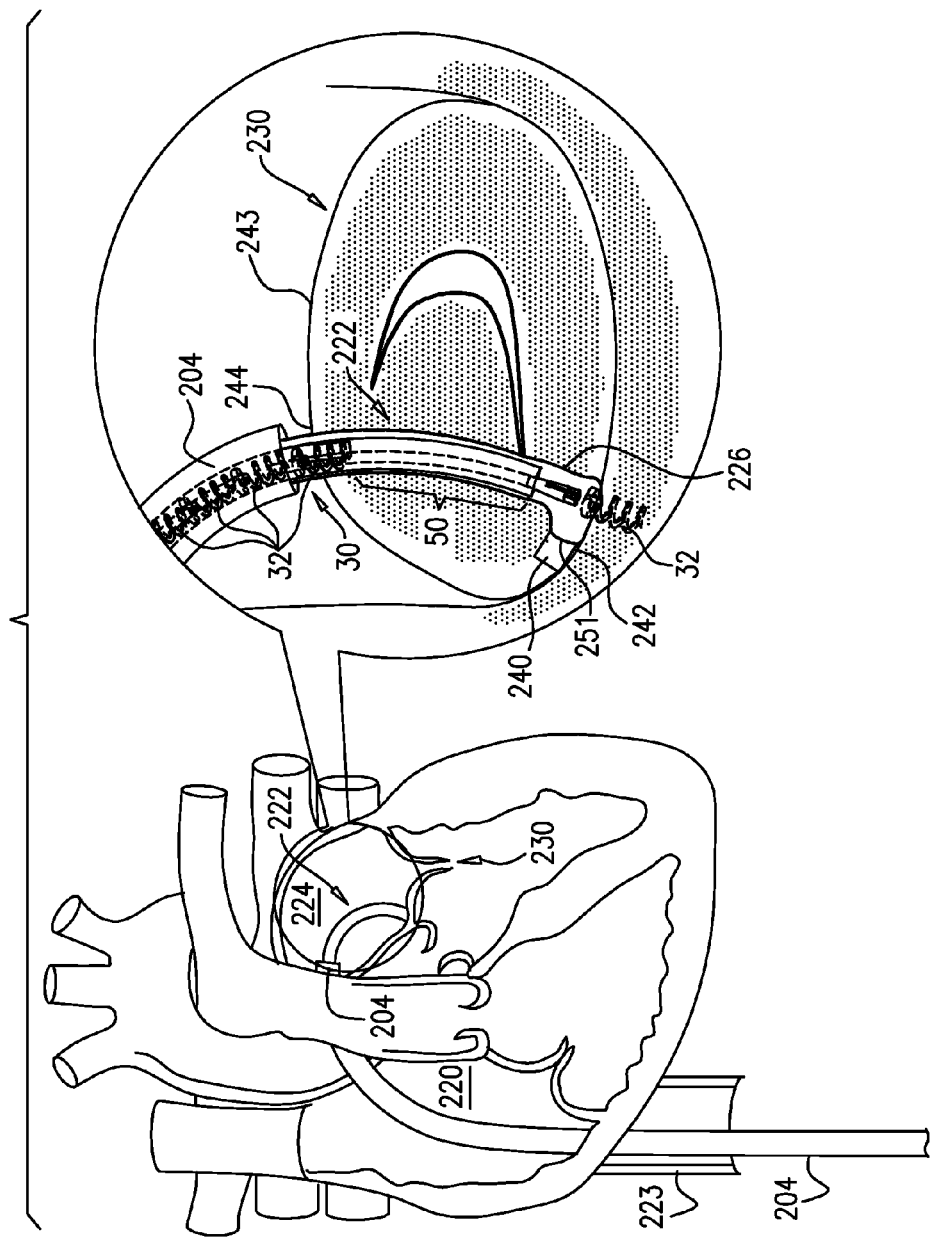

MULTIPLE ANCHOR DELIVERY TOOL

FIELD OF THE APPLICATION

Some embodiments of the present invention relate in general to surgical tools, and more specifically to surgical tools for delivering tissue anchors.

BACKGROUND OF THE APPLICATION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus. Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

U.S. Pat. No. 6,296,656 to Bolduc et al. describes a helical fastener having a high retentive surface area. The helical fastener has a first end for enhancing penetration into tissue and a second end comprising a coil sectioning a diameter of the fastener for receiving longitudinal and rotational forces. The helical fasteners are attached to body tissue by a fastener applicator having a proximal portion comprising a handle and an actuator and an elongate distal portion for housing a plurality of fasteners. A transferring action of the actuator provides longitudinal and rotational movement of the fasteners out of the distal portion and into body tissue.

U.S. Pat. No. 7,229,452 to Kayan describes a surgical tack for securing a surgical mesh material to body tissue. The tack includes a pair of legs and an arcuate cross-member. A surgical tack applier is also disclosed, for applying the surgical tack. The applier includes an elongate tubular portion having a jacket with a main channel and a pair of longitudinally extending sub-channels. A rotatable drive rod having a helical thread is coupled to the applier, and the sub-channels receive the legs of the tack. The helical thread receives the arcuate cross-member of the surgical tack. Rotation of the drive rod drives the tack from the distal end of the applier.

US Patent Application Publication 2007/0055206 to To et al. describes devices, methods, and kits for deployment of tissue anchors. In some variations, the devices comprise a shaft defining a lumen for housing at least one anchor therein (the anchor having an eyelet) and a mechanism for deploying the anchor distally from the lumen, wherein the inner diameter of the lumen is the same size or smaller than the diameter of the eyelet of the anchor to be disposed therein when the anchor is in an expanded configuration. In some variations, the methods comprise loading an anchor within a lumen of a shaft (where the anchor comprises an eyelet and the shaft has a slot therethrough), passing a linking member through the slot and through the eyelet of the anchor, and deploying the anchor. Other methods comprise loading an anchor within a lumen of a shaft, and deploying the anchor distally from the lumen.

US Patent Application Publication 2007/0080188 to Spence et al. describes systems and methods for securing tissue including the annulus of a mitral valve. The systems and methods may employ catheter based techniques and devices to plicate tissue and perform an annuloplasty. Magnets may be used for guidance in deploying fasteners from a catheter. The fasteners are cinched with a flexible tensile member.

US Patent Application Publication 2006/0241656 to Starksen et al. describes devices, systems and methods for facilitating positioning of a cardiac valve annulus treatment device, thus enhancing treatment of the annulus. Methods generally involve advancing an anchor delivery device through vasculature of the patient to a location in the heart for treating the valve annulus, contacting the anchor delivery device with a length of the valve annulus, delivering a plurality of coupled anchors from the anchor delivery device to secure the anchors to the annulus, and drawing the anchors together to circumferentially tighten the valve annulus. Devices generally include an elongate catheter having at least one tensioning member and at least one tensioning actuator for deforming a distal portion of the catheter to help it conform to a valve annulus. The catheter device may be used to navigate a subannular space below a mitral valve to facilitate positioning of an anchor delivery device.

US Patent Application Publication 2006/0025787 to Morales et al. describes methods and devices that provide constriction of a heart valve annulus to treat cardiac valve regurgitation and other conditions. Embodiments typically include a device for attaching a cinching or tightening apparatus to a heart valve annulus to reduce the circumference of the annulus, thus reducing valve regurgitation. Tightening devices may include multiple tethered clips, multiple untethered crimping clips, stabilizing devices, visualization devices, and the like. In one embodiment, a plurality of tethered clips is secured circumferentially to a valve annulus, and the tether coupling the clips is cinched to reduce the circumference of at least a portion of the annulus. Methods and devices may be used in open heart surgical procedures, minimally invasive procedures, catheter-based procedures, and/or procedures on beating hearts or stopped hearts.

US Patent Application Publication 2007/0016287 to Cartledge et al. describes an implantable device for controlling shape and/or size of an anatomical structure or lumen. The implantable device has an adjustable member configured to adjust the dimensions of the implantable device. The implantable device is housed in a catheter and insertable from a minimally invasive surgical entry. An adjustment tool actuates the adjustable member and provide for adjustment before, during or after the anatomical structure or lumen resumes near normal to normal physiologic function.

The following patents and patent application publications may be of interest:
U.S. Pat. No. 5,306,296 to Wright et al.
U.S. Pat. No. 5,674,279 to Wright et al.
U.S. Pat. No. 5,728,116 to Rosenman
U.S. Pat. No. 5,961,539 to Northrup, III et al.
U.S. Pat. No. 6,524,338 to Gundry
U.S. Pat. No. 6,569,198 to Wilson et al.
U.S. Pat. No. 6,602,288 to Cosgrove et al.
U.S. Pat. No. 6,602,289 to Colvin et al.
U.S. Pat. No. 6,619,291 to Hlavka et al.
U.S. Pat. No. 6,689,164 to Seguin
U.S. Pat. No. 6,702,826 to Liddicoat et al.
U.S. Pat. No. 6,718,985 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
U.S. Pat. No. 7,186,262 to Saadat
U.S. Pat. No. 7,431,692 to Zollinger et al.
U.S. Pat. No. 7,686,822 to Shayani US Patent Application Publication 2002/0087048 to Brock et al.
US Patent Application Publication 2002/0173841 to Ortiz et al.
US Patent Application Publication 2003/0050693 to Quijano et al.
US Patent Application Publication 2003/0167062 to Gambale et al.
US Patent Application Publication 2004/0024451 to Johnson et al.
US Patent Application Publication 2004/0122514 to Fogarty et al.
US Patent Application Publication 2004/0148021 to Cartledge et al.
US Patent Application Publication 2004/0236419 to Milo
US Patent Application Publication 2005/0171601 to Cosgrove et al.
US Patent Application Publication 2005/0055087 to Starksen
US Patent Application Publication 2005/0288781 to Moaddeb et al.
US Patent Application Publication 2006/0069429 to Spence et al.
US Patent Application Publication 2007/0051377 to Douk et al.
US Patent Application Publication 2007/0162111 to Fukamachi et al.
US Patent Application Publication 2007/0255400 to Parravicini et al.
US Patent Application Publication 2008/0004697 to Lichtenstein et al.
PCT Publication WO 01/26586 to Seguin
PCT Publication WO 02/085251 to Hlavka et al.
PCT Publication WO 02/085252 to Hlavka et al.
PCT Publication WO 06/097931 to Gross et al.
PCT Publication WO 07/136,783 to Cartledge et al.
PCT Publication WO 08/068,756 to Gross et al.
PCT Publication WO 10/004,546 to Gross et al.
The following articles may be of interest:
Brennan, Jennifer, "510(k) Summary of Safety and Effectiveness," January 2008
Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)
Odell J A et al., "Early Results of a Simplified Method of Mitral Valve Annuloplasty," Circulation 92:150-154 (1995)
O'Reilly S et al., "Heart valve surgery pushes the envelope," Medtech Insight 8(3): 73, 99-108 (2006)
Swain C P et al., "An endoscopically deliverable tissue-transfixing device for securing biosensors in the gastrointestinal tract," Gastrointestinal Endoscopy 40(6): 730-734 (1994)

SUMMARY OF THE APPLICATION

In some embodiments of the present invention, an anchor tissue deployment system comprises an anchor deployment tool and a plurality of tissue anchors. The anchor deployment tool comprises a flexible outer tube, a flexible inner shaft, which is positioned within the flexible outer tube, and a rotating deployment element, which is coupled to the distal end of the shaft. The anchor deployment tool is configured to provide an anchor storage area. The storage area initially stores the plurality of tissue anchors, such that the flexible inner shaft passes through channels that pass through each of the anchors, and the anchors are within the flexible outer tube. The rotating deployment element is configured to directly engage the anchors in the anchor storage area one at a time, advance each of the anchors while engaged in a distal direction, and deploy each of the anchors through the distal end of the outer tube and into tissue of a subject. Typically, the anchor deployment tool is configured to provide steering functionality to a distal anchor manipulation area of the anchor deployment tool between the anchor storage area and the distal tube end.

For some applications, the anchor deployment tool is configured such that, as the rotating deployment element advances each of the anchors in the distal direction, only the single anchor currently being advanced is within the distal anchor manipulation area of the anchor deployment tool. For some applications, the anchor deployment tool is configured to deploy each of the anchors into the tissue in a direction parallel to a central longitudinal axis of the outer tube through the distal tube end, and parallel to a central longitudinal axis of the anchor.

For some applications, the rotating deployment element is configured to pass through one or more of the anchors without engaging the anchors when the rotating deployment element is withdrawn in a proximal direction within the outer tube, and to directly engage one of the anchors when the rotating deployment element is advanced in the distal direction against the one of the anchors. Typically, the rotating deployment element is configured to assume a radially-compressed state when passing through the one or more of the anchors without engaging the anchors, and to assume a radially-expanded state when engaging the one of the anchors.

For some applications, the anchor deployment tool further comprises an anchor restraining mechanism in a vicinity of the distal anchor storage end. The mechanism is configured to temporarily restrain at least the distal-most anchor currently stored in the anchor storage area from advancing in the distal direction.

For some applications, each of the anchors comprises a helical tissue coupling element, and a tool-engaging head, fixed to one end of the tissue coupling element. The tool-engaging head is shaped so as to define an engaging opening that is at least partially non-circular, and that passes entirely through the tool-engaging head along the axis. The end of the tissue coupling element is fixed to the tool-engaging head near an outer perimeter of the tool-engaging head, such that the tissue coupling element does not block the engaging opening. The tissue coupling element and the tool-engaging head together define a channel along an entire length of the tissue anchor, which channel is sized and shaped such that a right circular cylinder could be placed within the channel, coaxial with the tissue anchor, and along the entire length of the tissue anchor. The cylinder typically has a diameter of at least 1 mm, such as at least 2 mm.

For some applications, the rotating deployment element is capable of unscrewing an already-deployed anchor from the tissue, withdrawing the anchor in a proximal direction, and subsequently redeploying the anchor into the tissue. For some applications, to enable such redeployment, the rotating deployment element is configured to selectively assume (a) a locked state, in which the rotating deployment element engages one of the anchors, such that the rotating deployment element can withdraw the anchor in the proximal direction, and (b) an unlocked state, in which the rotating deployment element does not engage the anchor.

For some applications, the anchor deployment system is used to deploy anchors for coupling an annuloplasty ring to tissue of a native cardiac valve of the subject, such as a mitral valve. For example, the annuloplasty ring may comprise a sleeve having a lumen, and the anchor deployment tool may be configured to be removably positioned within the lumen of the sleeve, and, while so positioned, to deploy the anchors from the distal tube end through a wall of the sleeve into the tissue. Alternatively applications for the anchor deployment system include delivery anchors via a working channel of an endoscope, such as to mount and secure a support mesh for treating a hernia.

There is therefore provided, in accordance with an application of the present invention, apparatus including:

a plurality of tissue anchors, which are shaped so as to define respective channels along entire longitudinal lengths of the anchors; and an anchor deployment tool, which includes:

a flexible outer tube, which has a distal tube end;

a flexible inner shaft, which is positioned within the flexible outer tube, and has a distal shaft end; and a rotating deployment element, which is coupled to the distal shaft end, wherein the anchor deployment tool is configured to provide an anchor storage area, which is configured to initially store the plurality of tissue anchors, such that the flexible inner shaft passes through the channels of the anchors, and the anchors are within the flexible outer tube, and wherein the rotating deployment element is configured to directly engage the anchors in the anchor storage area one at a time, advance each of the anchors while engaged in a distal direction, and deploy each of the anchors through the distal tube end and into tissue of a subject.

Typically, the anchor deployment tool is configured such that, as the rotating deployment element advances each of the anchors in the distal direction, only the single anchor currently being advanced is within a distal anchor manipulation area of the anchor deployment tool between the distal anchor storage area end and the distal tube end.

For some applications, the anchor deployment tool is configured to deploy each of the anchors into the tissue in a direction parallel to a central longitudinal axis of the outer tube through the distal tube end, and parallel to a central longitudinal axis of the anchor.

For some applications, the anchor storage area has a distal anchor storage end at a distance of between 1 and 90 cm from the distal tube end, such as between 5 and 25 cm.

For some applications, the anchor deployment tool is configured to provide steering functionality to a distal anchor manipulation area of the anchor deployment tool between the distal anchor storage area end and the distal tube end. For some applications, the flexible outer tube is configured to provide the steering functionality to the distal anchor manipulation area. Alternatively or additionally, the flexible inner shaft is configured to provide the steering functionality to the distal anchor manipulation area.

For some applications, the rotating deployment element is configured to pass through one or more of the anchors without engaging the anchors when the rotating deployment element is withdrawn in a proximal direction within the outer tube, and to directly engage one of the anchors when the rotating deployment element is advanced in the distal direction against the one of the anchors. Typically, the rotating deployment element is configured to assume a radially-compressed state when passing through the one or more of the anchors without engaging the anchors, and to assume a radially-expanded state when engaging the one of the anchors.

For some applications, the anchor deployment tool further includes a spring, which is arranged to apply a distally-directed force to a proximal-most one of the anchors stored within the anchor storage area, which force advances the anchors remaining in the anchor storage area in the distal direction, when the rotating deployment element advances a distal-most one of the anchors out of the anchor storage area in the distal direction. Alternatively, for some applications, the anchor storage area is configured to provide a plurality of anchor storage locations, the anchors are initially stored in respective ones of at least a portion of the anchor storage locations, and when the rotating deployment element advances a distal-most one of the anchors out of the anchor storage area in the distal direction, the anchors remaining in the anchor storage area remain in their respective initial anchor storage locations.

For some applications, the plurality of anchors includes at least 6 anchors.

For some applications, the anchor deployment tool further includes an anchor restraining mechanism in a vicinity of a distal end of the anchor storage area, which mechanism is configured to temporarily restrain at least a distal-most one of the anchors currently stored in the anchor storage area from advancing in the distal direction.

For some applications, each of the anchors has a central longitudinal axis, and includes:

a helical tissue coupling element, having proximal and distal ends; and a tool-engaging head, fixed to the proximal end of the tissue coupling element, which tool-engaging head is shaped so as to define a non-circular engaging opening that passes entirely through the tool-engaging head along the axis, wherein the tissue coupling element and the tool-engaging head together define the channel of the tissue anchor along an entire length of the tissue anchor, which channel is sized and shaped such that a right circular cylinder could be placed within the channel, coaxial with the tissue anchor, and along the entire length of the tissue anchor, and wherein the rotating coupling element is configured to removably engage the tool-engaging head.

For some applications, the cylinder has a diameter of at least 1 mm, such as at least 2 mm.

For some applications, the apparatus further includes an annuloplasty ring, which includes a sleeve having a lumen, and the anchor deployment tool is configured to be removably positioned within the lumen of the sleeve, and, while so positioned, to deploy the anchors from the distal tube end through a wall of the sleeve into the tissue.

For some applications, the distance between the distal anchor storage end and the distal tube end is between 5 and 25 cm.

For some applications, the anchor deployment tool further includes a hemostasis valve, which includes a distal port to which a proximal end of the flexible outer tube is sealingly coupled. The flexible inner shaft passes through the valve, which maintains a seal around the inner shaft, while allowing the inner shaft to slide distally and proximally through the valve.

For some applications, the rotating deployment element is capable of unscrewing an already-deployed one of the anchors from the tissue, withdrawing the anchor in a proximal direction, and subsequently redeploying the anchor into the tissue.

For some applications, the rotating deployment element includes a locking mechanism that is configured to selectively assume (a) a locked state, in which the locking mechanism, even upon withdrawal of the rotating deployment element in a proximal direction, prevents disengagement of the rotating deployment element from one of the anchors which the rotating deployment element engages, and (b) an unlocked state, in which the locking mechanism does not prevent disengagement of the rotating deployment element from the anchor upon the withdrawal of the rotating deployment element in the proximal direction.

There is further provided, in accordance with an application of the present invention, apparatus including a tissue anchor, which has a central longitudinal axis, and which includes:

a helical tissue coupling element, having proximal and distal ends; and a tool-engaging head, fixed to the proximal end of the tissue coupling element, which tool-engaging head is shaped so as to define a non-circular engaging opening that passes entirely through the tool-engaging head along the axis, wherein the tissue coupling element and the tool-engaging head together define a channel along an entire length of the tissue anchor, which channel is sized and shaped such that a right circular cylinder could be placed within the channel, coaxial with the tissue anchor, and along the entire length of the tissue anchor.

For some applications, the cylinder has a diameter of at least 1 mm, such as at least 2 mm.

For some applications, the proximal end of the tissue coupling element is fixed to the tool-engaging head near an outer perimeter of the tool-engaging head, such that the tissue coupling element does not block the engaging opening. For some applications, a distance between (a) a center of the proximal end of the tissue coupling element and (b) the outer perimeter of the tool-engaging head is no more than 30% of a width of the tool-engaging head.

For some applications, a portion of the helical tissue coupling element, at the proximal end which is fixed to the tool-engaging head, is generally straight and oriented at angle of between 0 and 15 degrees with the central longitudinal axis.

There is still further provided, in accordance with an application of the present invention, apparatus including:

a plurality of tissue anchors; and an anchor deployment tool, which (a) is configured to provide an anchor storage area that is configured to initially store the plurality of tissue anchors, and (b) includes a rotating deployment element, which is:

configured to directly engage the anchors in the anchor storage area one at a time, advance each of the anchors while engaged in a distal direction, and deploy each of the anchors through the distal tube end and into tissue of a subject by screwing the anchor into the tissue, and capable of unscrewing an already-deployed one of the anchors from the tissue, withdrawing the anchor in a proximal direction, and subsequently redeploying the anchor into the tissue.

For some applications, the rotating deployment element includes a locking mechanism that is configured to selectively assume (a) a locked state, in which the locking mechanism, even upon withdrawal of the rotating deployment element in the proximal direction, prevents disengagement of the rotating deployment element from one of the anchors which the rotating deployment element engages, and (b) an unlocked state, in which the locking mechanism does not prevent disengagement of the rotating deployment element from the anchor upon the withdrawal of the rotating deployment element in the proximal direction.

There is additionally provided, in accordance with an application of the present invention, a method including:

providing an anchor deployment tool, which includes a flexible outer tube, a flexible inner shaft, which is positioned within the flexible outer tube, and a rotating deployment element, which is coupled to a distal shaft end of the flexible inner shaft;

providing a plurality of tissue anchors, which are shaped so as to define respective channels along entire longitudinal lengths of the anchors, and which are initially stored within an anchor storage area provided by the anchor deployment tool, such that the flexible inner shaft passes through the channels of the anchors, and the anchors are within the flexible outer tube; and using the rotating deployment element, directly engaging the anchors in the anchor storage area one at a time, advancing each of the anchors while engaged in a distal direction, and deploying each of the anchors through the distal tube end and into tissue of a subject.

For some applications, advancing each of the anchors includes advancing each of the anchors in the distal direction such that only the single anchor currently being advanced is within a distal anchor manipulation area of the anchor deployment tool between the distal anchor storage area end and the distal tube end.

For some applications, deploying includes deploying each of the anchors into the tissue in a direction parallel to a central longitudinal axis of the outer tube through the distal tube end, and parallel to a central longitudinal axis of the anchor.

For some applications, deploying includes steering a distal anchor manipulation area of the anchor deployment tool between the distal anchor storage area end and the distal tube end.

For some applications, directly engaging, advancing, and deploying the anchors includes directly engaging, advancing, and deploying a first one of the anchors into the tissue at a first site; and, thereafter, directly engaging, advancing, and deploying a second one of the anchors into the tissue at a second site, different from the first site. For some applications, directly engaging the second anchor includes withdrawing the rotating deployment element in a proximal direction within the outer tube, such that the rotating deployment element passes through one or more of the anchors without engaging the anchors; and directly engaging the second anchor by advancing the rotating deployment element in the distal direction against the second anchor. For some applications, withdrawing includes withdrawing the rotating deployment element such that the rotating deployment element assumes a radially-compressed state when passing through the one or more of the anchors without engaging the anchors, and engaging includes engaging the second anchor when the rotating deployment element assumes a radially-expanded state.

For some applications, providing the plurality of anchors includes providing at least 6 anchors.

For some applications, deploying includes deploying each of the anchors into cardiac tissue of the subject. For some applications, deploying includes removably positioning the anchor deployment tool within a lumen of a sleeve of an annuloplasty ring, and, while so positioned, to deploying the anchors from the distal tube end through a wall of the sleeve into the tissue.

For some applications, providing the anchor deployment tool includes providing the anchor deployment tool in which the anchor storage area has a distal anchor storage end at a distance of between 1 and 90 cm from the distal tube end, such as between 5 and 25 cm.

For some applications, the method further includes, using the rotating deployment element, unscrewing an already-deployed one of the anchors from the tissue, withdrawing the anchor in a proximal direction, and subsequently redeploying the anchor into the tissue. For some applications, the rotating deployment element includes a locking mechanism that is configured to selectively assume a locked state, in which the locking mechanism, even upon withdrawal of the rotating deployment element in the proximal direction, prevents disengagement of the rotating deployment element from the anchor, the method further includes causing the locking mechanism to assume the locked state, and withdrawing the anchor includes withdrawing the anchor in the proximal direction while the rotating deployment element is in the locked state.

There is yet additionally provided, in accordance with an application of the present invention, a method including:

providing a tissue anchor having proximal and distal ends, which has a central longitudinal axis, and which includes a helical tissue coupling element, and a tool engaging head, fixed to the proximal end of the tissue coupling element, which tool-engaging head is shaped so as to define a non-circular engaging opening that passes entirely through the tool-engaging head along the axis, wherein the tissue coupling element and the tool-engaging head together define a channel along an entire length of the tissue anchor, which channel is sized and shaped such that a right circular cylinder could be placed within the channel, coaxial with the tissue anchor, and along the entire length of the tissue anchor; and coupling the tissue anchor to tissue of a subject, by rotating the tissue coupling element into the tissue.

For some applications, a distance between (a) a center of the proximal end of the tissue coupling element and (b) the outer perimeter of the tool-engaging head is no more than 30% of a width of the tool-engaging head, and coupling includes coupling a sheet to the tissue using the tissue anchor, sensing increased resistance to rotation of the tissue coupling element when the sheet resists the rotation, and, responsively the sensed increased resistance, ceasing rotating the tissue coupling element into the tissue.

There is also provided, in accordance with an application of the present invention, a method including:

providing a plurality of tissue anchors;

providing an anchor deployment tool, which (a) is configured to provide an anchor storage area, which is configured to initially store the plurality of tissue anchors, and (b) includes a rotating deployment element;

using the rotating deployment element, directly engaging the anchors in the anchor storage area one at a time, advancing each of the anchors while engaged in a distal direction, and deploying each of the anchors through the distal tube end and into tissue of a subject by screwing the anchor into the tissue; and subsequently, using the rotating deployment element, unscrewing an already-deployed one of the anchors from the tissue, withdrawing the anchor in a proximal direction, and subsequently redeploying the anchor into the tissue.

For some applications, the rotating deployment element includes a locking mechanism that is configured to selectively to assume a locked state, in which the locking mechanism, even upon withdrawal of the rotating deployment element in the proximal direction, prevents disengagement of the rotating deployment element from the anchor, the method further includes causing the locking mechanism to assume the locked state, and withdrawing the anchor includes withdrawing the anchor in the proximal direction while the rotating deployment element is in the locked state.

The present invention will be more fully understood from the following detailed description of embodiments thereof, taken together with the drawings, in which:

BRIEF DESCRIPTION OF THE DRAWINGS

FIGS. 1A-B are schematic illustrations of an anchor deployment system, in accordance with an application of the present invention;

FIGS. 2 and 3A-B are schematic illustrations showing the assembly of components of the anchor deployment system of FIGS. 1A-B, in accordance with an application of the present invention;

FIGS. 4A-D are schematic illustrations of the deployment of a single anchor into tissue using an anchor deployment tool of the anchor deployment system of FIGS. 1A-B, in accordance with an application of the present invention;

FIGS. 5A-B are schematic illustrations of an alternative configuration of the anchor deployment system of FIGS. 1A-B, in accordance with an application of the present invention;

FIGS. 6A-C are schematic illustrations of an anchor of the anchor deployment system of FIGS. 1A-B from three different views, in accordance with an application of the present invention;

FIGS. 7A and 7B are schematic illustrations of a rotating deployment element of the anchor deployment system of FIGS. 1A-B in radially-expanded and radially-compressed states, respectively, in accordance with an application of the present invention;

FIGS. 8A and 8B are schematic illustrations of the rotating deployment element of FIGS. 7A-B engaging a tool-engaging head of the anchor of FIGS. 6A-C, with the element in locked and unlocked states, respectively, in accordance with an application of the present invention; and FIGS. 9A-I are schematic illustrations of a procedure for implanting an annuloplasty ring to repair a mitral valve, in accordance with an application of the present invention.

DETAILED DESCRIPTION OF APPLICATIONS

Figure 9A:
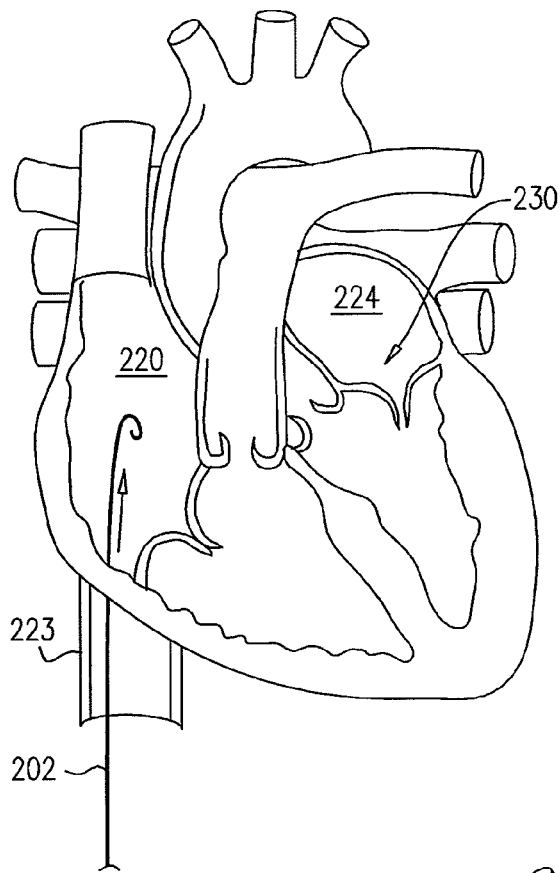

FIGS. 1A-B are schematic illustrations of an anchor deployment system 20, in accordance with an application of the present invention. Anchor deployment system 20 comprises an anchor deployment tool 30, which is configured to deliver a plurality of anchors 32 to respective sites within a body of a subject, and to couple the anchors to tissue at the sites. For some applications, tool 30 is configured to deploy anchors 32 to cardiac sites within the heart, such as in a vicinity of a valve annulus. Tool 30 comprises a flexible outer tube 34, within which is positioned a flexible inner shaft 36. Tool 30 further comprises a rotating deployment element 38, coupled to a distal shaft end 39 of inner shaft 36.

As shown in FIG. 1A, tool 30 (e.g., flexible outer tube 34) is configured to provide an anchor storage area 40, which is configured to initially store the plurality of anchors 32. The anchors are positioned within outer tube 34 such that inner shaft 36 passes through respective longitudinal channels of the anchors, as described hereinbelow with reference to FIGS. 6A-C. A distal anchor storage end 41 of anchor storage area 40 is typically at distance of at least 1 cm from a distal tube end 42 of outer tube 34, such as at least 3 cm or at least 5 cm, to enable flexibility and manipulation of the tool end. Distal anchor storage end 41 is typically at a distance of no more than 90 cm from distal tube end 42, such as no more than 25 cm, to maintain the comfort and stability level of the user. For some applications, distal anchor storage end 41 is at a distance of between 3 cm and 25 cm from distal tube end 42, such as between 5 cm and 25 cm. Tool 30 typically comprises a spring 44, which is arranged to apply a distally-directed force to the proximal-most anchor within anchor storage area 40, thereby holding the anchors within the storage area, and advancing the remaining anchors distally as each of the anchors is separately deployed.

The portion of tool 30 between distal anchor storage area end 41 and distal tube end 42 of outer tube 34 serves as a distal anchor manipulation area 50 of tool 30. Anchor manipulation area 50 is typically flexible and steerable. Typically, only one anchor at a time is deployed through anchor manipulation area 50 and into the tissue of the subject, such that no more than exactly one anchor is within anchor manipulation area 50 at any given time. As a result, anchor manipulation area 50 retains its flexibility. Because the anchors are typically rigid, when more than one of the anchors are longitudinally contiguously positioned within tool 30, the area of the tool in which the anchors are positioned becomes fairly stiff, substantially losing the flexibility it would otherwise have. Thus, while anchor storage area 40 is fairly rigid, anchor manipulation area 50 remains flexible because it only contains exactly one anchor at a given time. The stiffness of the area of the tool in which the anchors are positioned also may enable the user to better control the exact location of distal-most anchor 32 currently stored in anchor storage area 40.

The steering functionality of distal anchor manipulation area 50 typically allows the area near the distal end of tool 30 to be positioned with six degrees of freedom. For some applications, flexible outer tube 34 is configured to provide the steering functionality to distal anchor manipulation area 50. Flexible outer tube 34 comprises one or more steering wires, the pulling and releasing of which cause deflection of distal tube end 42, using deflection techniques known in the catheter art. Alternatively or additionally, flexible inner shaft 36 is configured to provide the steering functionality to distal anchor manipulation area 50. Flexible inner shaft comprises one or more steering wires for deflecting the distal end of the inner shaft. Still further alternatively or additionally, a separate flexible tube is provided for providing the steering functionality. The separate tube is positioned within flexible outer tube 34 or around the outer tube, and comprises one or more steering wires for deflecting the distal end of the inner shaft. The curvature of the tool may be pre-shaped, or bendable by application of an external force (such as a conventional colonoscope) or using an internal or external wire (configuration not shown). For some applications, the steering functionality is provided by a combination of more than one of flexible outer tube 34, flexible inner shaft 36, and the separate flexible tube, e.g., by (a) flexible outer tube 34 and flexible inner shaft 36, (b) flexible outer tube 34 and the separate flexible tube, (c) flexible inner shaft 36 and the separate flexible tube, or (d) all of flexible outer tube 34, flexible inner shaft 36, and the separate flexible tube.

For some applications, an external control handle is provided for controlling tool 30. The control handle comprises circuitry for manipulating the steering wires to provide the steering functionality.

For some applications, flexible inner shaft 36 comprises stainless steel SS 304, Nitinol, PEEK®, polyester, or another polymer. For some applications, outer tube 34 comprises stainless steel SS 304, Nitinol, PEEK®, polyester, or another polymer. For some applications, flexible inner shaft 36 has a diameter of at least 0.8 mm, no more than 3 mm, and/or between 0.8 and 3 mm, such as between 1 and 2 mm. For some applications, outer tube 34 has an outer diameter of at least 2 mm, no more than 4 mm, and/or between 2 and 4 mm, e.g., 3 mm or 3.2 mm. For some applications, outer tube 34 has an inner diameter of at least 1.5 mm, no more than 3.5 mm, and/or between 1.5 and 3.5 mm, e.g., 2.6 mm.

For some applications, anchor deployment tool 30 further comprises a hemostasis valve 80, as shown in FIG. 1B. Hemostasis valve 80 minimizes leakage of blood, and entrance of air (thereby reducing the risk of air emboli), during a percutaneous procedure performed using system 20. A proximal end of flexible outer tube 34 is sealingly coupled to a distal port of valve 80. Inner shaft 36 passes through valve 80, which maintains a seal around the inner shaft, while allowing the inner shaft to slide distally and proximally through the valve during deployment of anchors 32, as described hereinbelow with reference to FIGS. 4A-D. Valve 80 optionally comprises a side port 82 for flushing the system, as is known in the hemostasis valve art. For other applications, the anchor deployment tool does not comprise the hemostasis valve.

Reference is made to FIGS. 2 and 3A-B, which are schematic illustrations showing the assembly of components of anchor deployment system 20, in accordance with an application of the present invention. Typically, spring 44 is positioned around a proximal portion of flexible inner shaft 36. A distal end 58 of the spring applies a force in a distal direction against the proximal end of the proximal-most anchor 32 (right-most in the figures) stored in anchor storage area 40. The plurality of anchors 32 are initially positioned end-to-end longitudinally contiguously around flexible inner shaft 36 within anchor storage area 40. By way of example, FIG. 2 shows five anchors 32. Typically, system 20 is configured to store between 6 and 20 anchors 32, such as between 8 and 16 anchors 32.

As shown in the blow-up of FIG. 2, and described in more detail hereinbelow with reference to FIGS. 6A-C, each of anchors 32 comprises a helical tissue coupling element 60, and a tool-engaging head 62, fixed to one end of the tissue coupling element. Rotating deployment element 38 is configured to removably engage tool-engaging head 62, as described in more detail hereinbelow with reference to FIGS. 4A-D and 6A-C.

For some applications, tool 30 provides an anchor restraining mechanism 70 in a vicinity of distal anchor storage area end 41. Anchor restraining mechanism 70 is configured to temporarily restrain at least the distal-most anchor 32 currently stored in anchor storage area 40 from advancing in a distal direction as another one of the anchors is deployed through anchor manipulation area 50 and into the tissue of the subject. Optionally, anchor restraining mechanism 70 is also configured to temporarily restrain at least the distal-most anchor 32 from withdrawing in a proximal direction as inner shaft 36 is withdrawn in the proximal direction to load a subsequent one of the anchors.

For some applications, as shown in the blow-up of FIG. 3A, anchor restraining mechanism 70 comprises one or more distal tabs 72 for temporarily restraining the distal-most anchor 32 currently stored in anchor storage area 40 from advancing in the distal direction. The distal tabs may be cut out of flexible outer tube 34, as shown, or they may be provided as separate elements coupled to the outer tube. The distal tabs apply a force in a radially-inward direction against a distal portion of anchor 32, gently squeezing against the distal portion. The force is sufficient to prevent distal motion of distal-most anchor 32 and the other anchors currently stored in anchor storage area 40, which otherwise would be advanced distally by the force applied on the proximal-most anchor 32 by spring 44. However, the force is insufficient to prevent distal advancement of distal-most anchor 32 when the anchor is engaged and advanced distally by rotating deployment element 38, as described hereinbelow with reference to FIGS. 4A-B. For some applications, anchor restraining mechanism 70 comprises two distal tabs 72, typically on opposite sides of the outer tube (typically axially aligned with each other), as shown, while for other applications, the anchor restraining mechanism comprises exactly one distal tab, or three or more distal tabs, e.g., three or four distal tabs (typically axially aligned with one another).

For some applications, anchor restraining mechanism 70 comprises a set 73 of one or more proximal tabs 74 for temporarily restraining the distal-most anchor 32 currently stored in anchor storage area 40 from withdrawing in the proximal direction. The proximal tabs may be cut out of flexible outer tube 34, as shown, or they may be provided as separate elements coupled to the outer tube. The distal ends of the proximal tabs engage the proximal end of the tool-engaging head of distal-most anchor 32. For some applications, set 73 comprises two proximal tabs 74, typically on opposite sides of the outer tube (typically axially aligned with each other), as shown, while for other applications, the set comprises exactly one proximal tab, or three or more proximal tabs, e.g., three or four proximal tabs (typically axially aligned with one another).

Reference is made to FIGS. 4A-D, which are schematic illustrations of the deployment of a single one of anchors 32 into tissue using anchor deployment tool 30, in accordance with an application of the present invention. As shown in FIG. 4A, the anchor to be deployed is the distal-most one of the anchors stored in anchor storage area 40, and is initially restrained in the anchor storage area by anchor restraining mechanism 70. Flexible inner shaft 36 is advanced in a distal direction until rotating deployment element 38 directly engages tool-engaging head 62 of the anchor (by "directly engages," it is meant that rotating deployment element 38 comes in direct contact with the anchor, rather than indirect contact via one or more of the other anchors). Rotating deployment element 38 assumes its radially-expanded state, as described hereinbelow with reference to FIG. 7A, to enable this engagement.

As shown in FIG. 4B, flexible inner shaft 36 is advanced in the distal direction, until rotating deployment element 38 brings the anchor into contact with tissue 90 of a subject at a first site. For example, the tissue may be cardiac tissue. Typically, anchor deployment tool 30 is configured such that, as rotating deployment element 38 advances each of the anchors in the distal direction, only the single anchor 32 currently being advanced is within distal anchor manipulation area 50. Rotating deployment element 38 is rotated, in order to screw helical tissue coupling element 60 of the anchor into the tissue. For some applications, rotating deployment element 38 is rotated by rotating flexible inner shaft 36. For other applications, rotating deployment element 38 is rotated by rotating an additional rotation shaft provided within flexible inner shaft 36, which additional shaft is coupled to rotating deployment element 38. Rotation of rotating deployment element 38 typically rotates only the anchor currently engaged by the deployment element, while the other anchors still stored in the storage area typically are not rotated.

Typically, anchor 32 is deployed from distal tube end 42 of outer tube 34 of tool 30 into cardiac tissue 90 in a direction parallel to a central longitudinal axis 92 of outer tube 34 through distal tube end 42, and/or parallel to central longitudinal axis 100 of anchor 32, as described hereinbelow with reference to FIGS. 6A-C.

Also as shown in FIG. 4B, the evacuation of the distal-most anchor from anchor restraining mechanism 70 frees up the anchor restraining mechanism for the next distal-most anchor remaining in anchor storage area 40. Spring 44 distally advances all of anchors 32 remaining in anchor storage area 40, until the next distal-most anchor is positioned within anchor restraining mechanism 70.

As shown in FIG. 4C, after the anchor has been coupled to tissue 90, rotating deployment element 38 is disengaged from the anchor by withdrawing the rotating deployment element in a proximal direction. As the rotating deployment element passes through the next anchor in the proximal direction, the rotating deployment element is squeezed by the engaging opening of tool-engaging head 62 of the next anchor, causing the rotating deployment element to assume its radially-compressed state, as described hereinbelow with reference to FIG. 7B.

As shown FIG. 4D, anchor deployment tool 30 is repositioned to deploy a second anchor 32 at a second site of tissue 90, different from the first site. Such repositioning is typically accomplished using the steering functionality of distal anchor manipulation area 50, as described hereinabove. The steps of the deployment method are repeated, until as many anchors 32 as desired have been deployed, at respective sites, e.g., a first site, a second site, a third site, a fourth site, etc.

Reference is made to FIGS. 5A-B, which are schematic illustrations of an alternative configuration of anchor deployment system 20, in accordance with an application of the present invention. In this configuration, anchor restraining mechanism 70 typically comprises one or more distal tabs 72, as in the configuration described hereinabove with reference to FIGS. 2, 3A-B, and 4A-D. Unlike in the configuration described hereinabove with reference to FIGS. 2, 3A-B, and 4A-D, in this configuration anchor restraining mechanism 70 comprises a plurality of sets 73 of proximal tabs 74, labeled 73A, 73B, 73C, . . . in FIGS. 5A-B. Each set of proximal tabs engages exactly one anchor 32. For example, the distal ends of proximal tabs 74 of set 73A engage the proximal end of the tool-engaging head of distal-most anchor 32, and the distal ends of proximal tabs 74 of set 73B engage the proximal end of the tool-engaging head of second-to-distal-most anchor 32.

Sets 73 thus provide respective anchor storage locations. Therefore, the anchor restraining mechanism comprises a number of sets 73 greater than or equal to the number of anchors 32 initially stored in anchor storage area 40. For some applications, anchor restraining mechanism 70 comprises between 6 and 20 sets 73, such as between 8 and 16 sets 73. For some applications, each of sets 73 comprises two proximal tabs 74, typically on opposite sides of the outer tube (typically axially aligned with each other), as shown, while for other applications, each of the sets comprises exactly one proximal tab, or three or more proximal tabs, e.g., three or four proximal tabs (typically axially aligned with one another).

For some applications, each of sets 73 (except the proximal-most set 73) additionally functions as a distal tab 72 for the anchor proximally adjacent to the set. For example, set 73A, in addition to engaging distal-most anchor 32A, also prevents distal motion of second-to-distal-most anchor 32.

Unlike in the configuration described hereinabove with reference to FIGS. 2, 3A-B, and 4A-D, in the present configuration each of anchors 32 remains in place in its initial, respective anchor storage location in anchor storage area 40, until the anchor is individually advanced out of anchor storage area 40 during deployment by anchor deployment tool 30. Spring 44 is thus typically not provided in this configuration. Deployment of the anchors is typically performed as described hereinabove with reference to FIGS. 4A-D, except:

at the step described with reference to FIG. 4B, spring 44 does not distally advance the remaining anchors (as mentioned above, spring 44 is typically not provided in this configuration); and at the step described with reference to FIG. 4C, anchor deployment tool 30 is withdrawn further proximally, until the anchor deployment tool reaches the next remaining anchor 32 in anchor storage area 40. The next anchor, as mentioned above, has remained in its original location even after deployment of more distally positioned anchor(s) 32.

Reference is now made to FIGS. 6A-C, which are schematic illustrations of one of anchors 32 from three different views, in accordance with an application of the present invention. As described above, each of anchors 32 comprises helical tissue coupling element 60, and tool-engaging head 62, fixed to one end of the tissue coupling element (the proximal end of the tissue coupling element, opposite the distal end that first penetrates the tissue). Anchor 32 comprises a hard material, such as metal, e.g., steel, Nitinol, or stainless steel SS316LVM. Anchor 32 may be manufactured from a single piece of material, or coupling element 60 and tool-engaging head 62 may be manufactured from separate pieces of material and fixed together.

Typically, helical tissue coupling element 60 has an inner diameter D1 of at least 1.5 mm, no more than 2.5 mm, and/or between 1.5 and 2.5 mm, e.g., 1.8 mm, along an entire length thereof along a central longitudinal axis 100 of anchor 32 (although inner diameter D1 is shown as being constant along the entire length of coupling element 60, the inner diameter optionally varies along the length of the coupling element). Inner diameter D1 is sufficiently large to allow passage through helical tissue coupling element 60 of flexible inner shaft 36 and rotating deployment element 38, optionally even when rotating deployment element 38 is in its radially-expanded state, as described hereinbelow with reference to FIG. 7A. An outer diameter D2 of helical tissue coupling element 60 may be, for example, at least 2.4 mm, no more than 5 mm, and/or between 2.4 and 5 mm, e.g., 2.4 mm.

Tool-engaging head 62 is shaped so as to define an engaging opening 102 that passes entirely through the tool-engaging head along axis 100. The engaging opening is typically at least partially non-circular, in order to engage rotating deployment element 38. For example, as shown in FIGS. 6A-C, engaging opening 102 may be shaped so as to define a proximal non-circular internal engaging surface 66, and a distal circular non-engaging surface 64. Proximal engaging surface 66 is shaped to engage rotating deployment element 38, such that rotation of the deployment element rotates tool-engaging head 62 and anchor 32. For example, proximal engaging surface 66 may be rectangular (e.g., square), teethed (e.g., defining a plurality of squares with which rotating element 38 can engage, for applications in which engaging elements 120A and 120B together have a square cross-sectional shape), star-shaped, polygonal (e.g., octagonal), or any other appropriate non-circular shape.

A portion of deployment element 38 may pass partially or completely through distal non-engaging surface 64, without engaging this surface. The non-engaging surface may serve as a shoulder, which pushes against tissue 90, providing resistance when the anchor has been sufficiently screwed into the tissue. Optionally, deployment element 38 does not pass entirely through distal non-engaging surface 64, such that the deployment element does not press against or into the tissue. Alternatively, the deployment element may protrude slightly from the distal non-engaging surface 64, as shown in FIGS. 8A-B, when no force is applied to the deployment element by the tissue. Optionally, when the anchor is pressed against the tissue, inner spaces in the tool-engagement head 62 of the anchor allow the deployment element to sink into the anchor, and not press against the tissue.

Engaging opening 102 typically has a cross-sectional area (perpendicular to axis 100) of at least 0.8 mm2, such as at least 1.2 mm2. The area is sufficient large to allow passage through engaging opening 102 of flexible inner shaft 36 and rotating deployment element 38, when the rotating deployment element assumes its radially-compressed state by being withdrawn in a proximal direction (from tissue coupling element 60 toward tool-engaging head 62), as described hereinbelow with reference to FIG. 7B.

For some applications, the anchor is used to couple a sheet of material, such as a fabric, to tissue 90. For these applications, because the tissue coupling element is fixed near the edge of the tool-engaging head, the sheet resists further rotation of the anchor once the anchor is fully screwed into the tissue and the tool-engaging head contacts the sheet. Such resistance prevents accidental over-rotation of the anchor, which could tear the tissue or the sheet. In contrast, in anchors in which the tissue coupling element is fixed at or near the center of the tool-engaging head, the sheet does not resist rotation of the anchor after the anchor has been fully screwed into the tissue and the tool-engaging head contacts the sheet. For some applications, the surgeon or a sensor sense increased resistance to rotation of the tissue coupling element when the sheet resists the rotation, and, responsively the sensed increased resistance, the surgeon ceases rotating the tissue coupling element into the tissue For some applications, anchor deployment system 20 comprises a torque-limiting element, as is known for conventional screwdrivers, to prevent over-application of torque. Alternatively or additionally, for some applications, anchor deployment system 20 comprises a sensor (e.g., a torque transducer), for measuring the resistance to rotation of anchor 32. When the measured resistance exceeds a threshold value, the system generates a signal alerting the surgeon, and/or discontinues rotation of inner shaft 36. The increased resistance is typically caused by the sheet, as described above, and/or the non-engaging surface (shoulder) of the anchor head, as described above.

For some applications, a proximal-most portion 106 of helical tissue coupling element 60, at the end which is fixed to tool-engaging head 62, is generally straight and oriented generally parallel to axis 100, i.e., at angle of between 0 and 15 degrees with the axis, such as degrees. Proximal-most portion 106 typically has a length of between 0.5 and 2 mm, such as about 1 mm.

The outer perimeter of tool-engaging head 62 is typically circular, and an outer diameter D3 of tool-engaging head 62 may be, for example, at least 2 mm, no more than 7 mm, and/or between 2 and 7 mm, such as between 2.5 and 5 mm, e.g., 2.4 mm, 2.5 mm, or 3 mm.

The outer diameter of anchor 32 is typically equal to outer diameter D3 of tool-engaging head 62, or, alternatively, to outer diameter D2 of coupling element 60. The outer diameter of anchor 32 may be, for example, at least 2 mm, no more than 7 mm, and/or between 2 and 7 mm, such as between 2.5 and 5 mm. The entire length of anchor 32, measured along axis 100, is typically at least 2.5 mm, no more than 6 mm, and/or between 2.5 and 6 mm, such as between 3 and 4.5 mm.

The proximal end of tissue coupling element 60 is typically fixed to tool-engaging head 62 near the outer perimeter of the tool-engaging head, such that the tissue coupling element does not block engaging opening 102. For example, as labeled in the top-view of the anchor in FIG. 6C, the tissue coupling element may be fixed to the tool-engaging head such that one or more of the following dimension characterize the anchor:

- a distance D5 between (a) a center 110 of the proximal end of tissue coupling element 60 and (b) an outer perimeter of tool-engaging head 62 is no more than 20% of a width D3 of tool-engaging head 62 (the width is a diameter for applications in which the head is circular), such as no more than 10% of width D3. For example, distance D5 may be between 0.1 and 0.3 mm, e.g., 0.2 mm;
- a distance D6 between (a) a most radially-inward portion 112 of the proximal end of tissue coupling element 60 (i.e., the portion of the proximal end that is closest to central longitudinal axis 100 of the anchor) and (b) the outer perimeter of tool-engaging head 62 is no more than 40% of width D3 of tool-engaging head 62 (the width is a diameter for applications in which the head is circular), such as no more than 30% of width D3, or no more than 20% of width D3. For example, distance D6 may be between 0.3 and 0.5 mm, e.g., 0.4 mm; and/or
- a distance between (a) a most radially-outward portion 114 of the proximal end of tissue coupling element 60 (i.e., the portion of the proximal end that is furthest from central longitudinal axis 100 of the anchor) and (b) the outer perimeter of tool-engaging head 62 is no more than 10% of width D3 of tool-engaging head 62 (the width is a diameter for applications in which the head is circular), such as no more than 5% of width D3, e.g., 0. For example, distance D6 may be between 0 and 0.1 mm, e.g., 0 mm.

Anchor 32, including both helical tissue coupling element 60 and tool-engaging head 62, is thus shaped so as to provide a channel along the entire length of the anchor, through which flexible inner shaft 36 can pass, and through which rotating deployment element 38 can pass when in its radially-compressed state, as described hereinabove with reference to FIGS. 1A-4D. More generally, as shown in FIG. 6B, the channel is sized and shaped such that a right circular cylinder 104 could be placed within the channel, coaxial with anchor 32 (i.e., the axis of the cylinder coincides with central longitudinal axis 100 of anchor 32), and along the entire length of the tissue anchor, the cylinder having a diameter D4 of at least 1 mm, such as at least 2 mm. Typically, diameter D4 is between 0.05 and 1 mm greater than diameter D3 of tool-engaging head 62. It is to be understood that cylinder 104 is an abstract geometric shape, rather than an element of an embodiment of the invention, and, as such, is perfectly cylindrical, i.e., is not shaped so as to define any grooves or other surface or internal anomalies. No portion of anchor 32 intersects central longitudinal axis 100.

Reference is made to FIGS. 7A and 7B, which are schematic illustrations of rotating deployment element 38 in radially-expanded and radially-compressed states, respectively, in accordance with an application of the present invention. For some applications, rotating deployment element 38 is shaped so as to define at least two prongs 124A and 124B that extend in a distal direction from a proximal base 122 of the deployment element. Engagement elements 120A and 120B extend in a distal direction from prongs 124A and 124B, respectively. The engagement elements are typically male, and, for example, may together have a cross-sectional shape that is rectangular, e.g., square. Optionally, rotating deployment element 38 comprises more than two prongs and two engagement elements, e.g., three or four of each.

Rotating deployment element 38 is typically configured to assume a radially-expanded state as its resting state, as shown in FIG. 7A. In this expanded state, engagement elements 120A and 120B, as well as prongs 124A and 124B, are positioned apart from one another. In this state, the engagement elements are shaped and sized to engage tool-engaging head 62 of anchor 32, as shown, for example, in FIG. 4B.

As shown in FIG. 7B, the rotating deployment element 38 assumes a radially-compressed state, when the engagement elements and prongs are squeezed together, such as by passing through the engaging opening of tool-engaging head 62 of anchor 32, as described hereinabove with reference to FIG. 4C.

Reference is now made to FIGS. 8A and 8B, which are schematic illustrations of rotating deployment element 38 engaging tool-engaging head 62 of anchor 32, with the element 38 in locked and unlocked states, respectively, in accordance with an application of the present invention. In accordance with this application, rotating deployment element 38 comprises a locking mechanism 128, which is configured to selectively assume locked and unlocked states. When locking mechanism 128 assumes the locked state, the locking mechanism prevents disengagement of rotating deployment element 38 from the anchor which rotating deployment element 38 currently engages anchor. This locking allows deployment element 38 to proximally withdraw anchor 32 if necessary, without coming disengaged therefrom. Disengagement is thus prevented even upon withdrawal of the rotating deployment element in the proximal direction. When the locking mechanism assumes the unlocked state, the locking mechanism does not prevent disengagement of the rotating deployment element from the anchor upon withdrawal of rotating deployment element 38 in the proximal direction. The rotating deployment element thus can be disengaged and withdrawn from the anchor in a proximal direction. It is noted that even when the locking mechanism assumes the unlocked state, the rotating deployment element generally does not disengage from the anchor unless the rotating deployment element is withdrawn in the proximal direction. As mentioned above with reference to FIG. 7A, rotating deployment element 38 is typically configured to assume a radially-expanded state as its resting state. In this radially-expanded state, engagement elements 120A and 120B are positioned apart from each other, and engage tool-engaging head 62 of anchor 32.

For some applications, locking mechanism 128 comprises a pin 130. In order to cause the locking mechanism to assume the locked position, pin 130 is advanced distally between engagement elements 120A and 120B. The pin holds the engagement elements in their radially-expanded state, as described hereinabove with reference to FIG. 7A, thereby preventing the engagement elements from assuming the radially-compressed state shown in FIG. 7B and disengaging from the anchor. In the radially-expanded state, the engagement elements engage proximal engaging surface 66 of tool-engaging head 62 of anchor 32. In order to cause locking mechanism 128 to assume the unlocked state, pin 130 is withdrawn proximally from between engagement elements 120A and 120B. As a result, the engagement elements may assume the radially-compressed state shown in FIG. 7B when deployment element 38 is withdrawn in the proximal direction. In the radially-compressed state, the engagement elements do not engage the tool-engaging head of the anchor.

Providing this selective, actively-controllable engagement and release of the anchor allows rotating deployment element 38 to be used to unscrew an already-deployed anchor from the tissue, and/or to proximally withdraw an anchor, without deployment element 38 unintentionally disengaging from the anchor head. Such unscrewing or proximal withdrawal may allow an anchor to be repositioned if it is initially coupled to the tissue in an incorrect location. Rotating deployment element 38 is capable of performing this redeployment for both (a) the anchor that has been most recently deployed into the tissue, and to which the deployment element 38 is still coupled, and (b) an anchor that was previously deployed, and from which deployment element 38 has already been decoupled (and, optionally, even after another anchor has subsequently been deployed). In the latter case, deployment element 38 re-engages the anchor that is to be redeployed.

Reference is now made to FIGS. 9A-I, which are schematic illustrations of a procedure for implanting an annuloplasty ring 222 to repair a mitral valve 230, in accordance with an application of the present invention. This procedure is one exemplary procedure that can be performed using anchor deployment system 20.

Annuloplasty ring 222 is used to repair a dilated valve annulus of an atrioventricular valve, such as mitral valve 230. For some applications, the annuloplasty ring is configured to be placed only partially around the valve annulus (e.g., to assume a C-shape), and, once anchored in place, to be contracted so as to circumferentially tighten the valve annulus. The annuloplasty ring comprises a flexible sleeve 226 and a plurality of anchors 32. Anchor deployment tool 30 is advanced into a lumen of sleeve 226, and, from within the lumen, deploys the anchors through a wall of the sleeve and into cardiac tissue, thereby anchoring the sleeve around a portion of the valve annulus. For some applications, annuloplasty ring 222 is implemented using techniques described in U.S. application Ser. No. 12/437,103, filed May 7, 2009 which published as US 2010/0286767, and/or U.S. application Ser. No. 12/689,635, filed Jan. 19, 2010 which published as US 2010/0280604, both of which are assigned to the assignee of the present application and are incorporated herein by reference. For some application, annuloplasty ring 222 comprises a contracting mechanism 240. The contracting mechanism comprises a rotatable structure, such as a spool, arranged such that rotation of the rotatable structure contracts the implant structure. The implant further comprises a longitudinal member, such as a wire, which is coupled to the contracting mechanism. A rotation tool is provided for rotating the rotatable structure. The tool is configured to be guided along (e.g., over, alongside, or through) the longitudinal member, to engage the rotatable structure, and to rotate the rotatable structure in response to a rotational force applied to the tool.

As shown in FIG. 9A, the procedure typically begins by advancing a semi-rigid guidewire 202 into a right atrium 220 of the patient. The procedure is typically performed with the aid of imaging, such as fluoroscopy, transesophageal echo, and/or echocardiography.

Figure 9B:
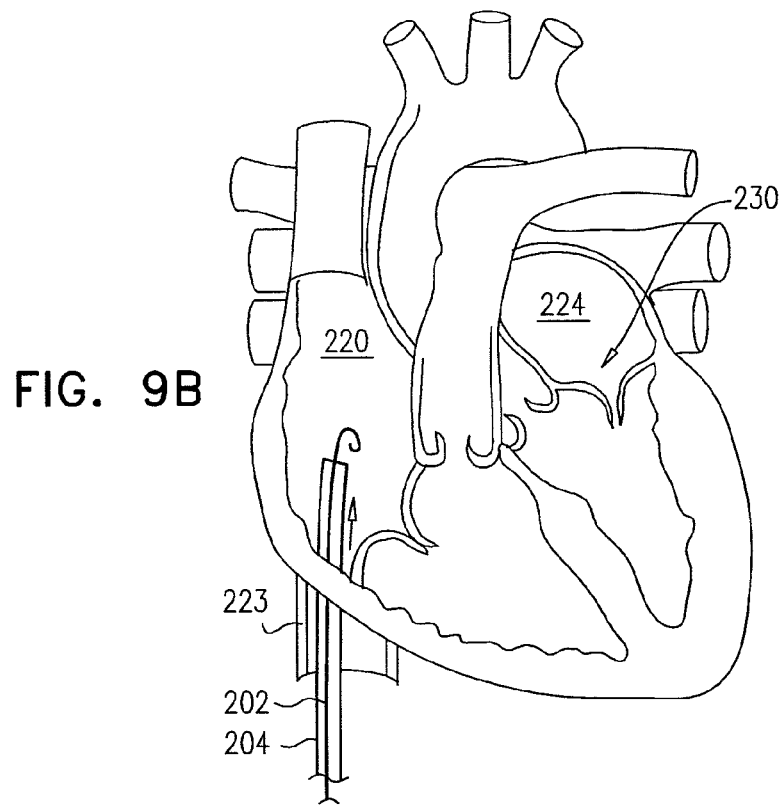

As show in FIG. 9B, guidewire 202 provides a guide for the subsequent advancement of a sheath 204 therealong and into the right atrium. Once sheath 204 has entered the right atrium, guidewire 202 is retracted from the patient's body. Sheath 204 typically comprises a 14-20 F sheath, although the size may be selected as appropriate for a given patient. Sheath 204 is advanced through vasculature into the right atrium using a suitable point of origin typically determined for a given patient. For example:

sheath 204 may be introduced into the femoral vein of the patient, through an inferior vena cava 223, into right atrium 220, and into a left atrium 224 transseptally, typically through the fossa ovalis;

sheath 204 may be introduced into the basilic vein, through the subclavian vein to the superior vena cava, into right atrium 220, and into left atrium 224 transseptally, typically through the fossa ovalis; or sheath 204 may be introduced into the external jugular vein, through the subclavian vein to the superior vena cava, into right atrium 220, and into left atrium 224 transseptally, typically through the fossa ovalis.

For some applications of the present invention, sheath 204 is advanced through inferior vena cava 223 of the patient (as shown) and into right atrium 220 using a suitable point of origin typically determined for a given patient.

Figure 9C:
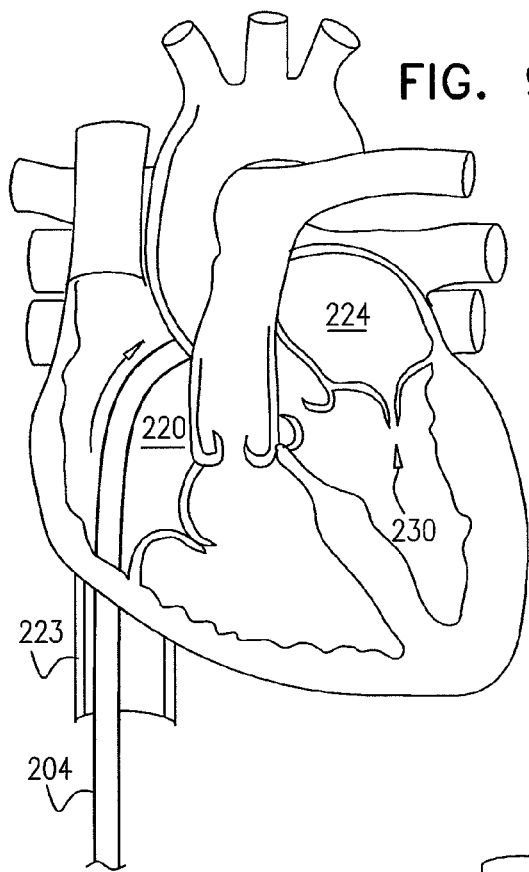

Sheath 204 is advanced distally until the sheath reaches the interatrial septum, and guidewire 202 is withdrawn, as shown in FIG. 9C.

Figure 9D:
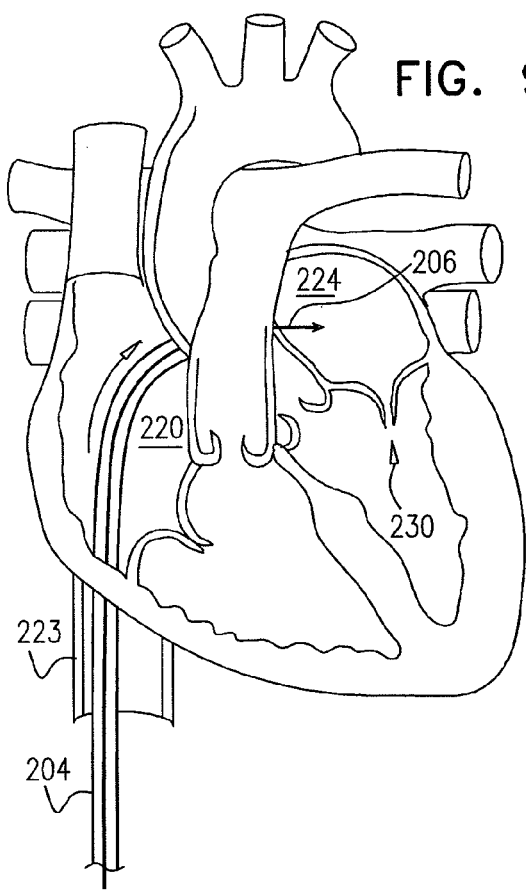

As shown in FIG. 9D, a resilient needle 206 and a dilator (not shown) are advanced through sheath 204 and into the heart. In order to advance sheath 204 transseptally into left atrium 224, the dilator is advanced to the septum, and needle 206 is pushed from within the dilator and is allowed to puncture the septum to create an opening that facilitates passage of the dilator and subsequently sheath 204 therethrough and into left atrium 224. The dilator is passed through the hole in the septum created by the needle. Typically, the dilator is shaped to define a hollow shaft for passage along needle 206, and the hollow shaft is shaped to define a tapered distal end. This tapered distal end is first advanced through the hole created by needle 206. The hole is enlarged when the gradually increasing diameter of the distal end of the dilator is pushed through the hole in the septum.

Figure 9E:
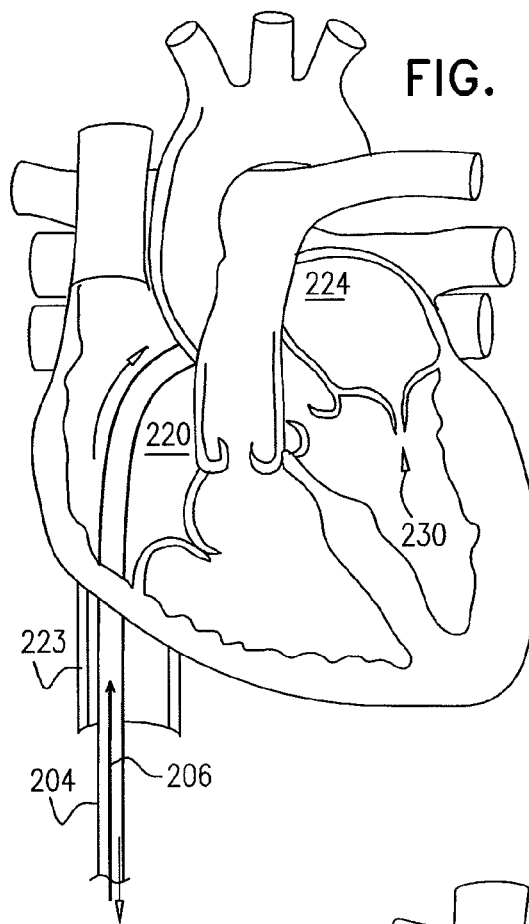

The advancement of sheath 204 through the septum and into the left atrium is followed by the extraction of the dilator and needle 206 from within sheath 204, as shown in FIG. 9E.

Figure 9F:
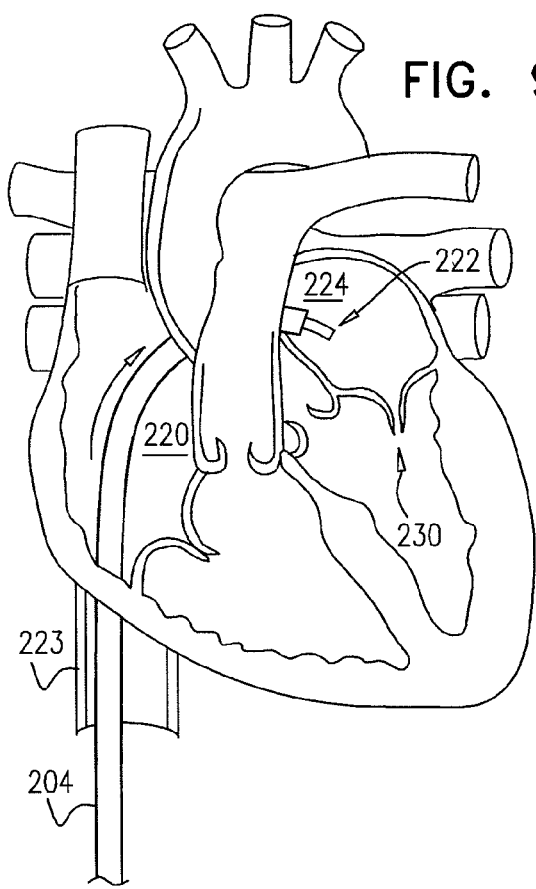

As shown in FIG. 9F, annuloplasty ring 222 (with anchor deployment tool 30 therein) is advanced through sheath 204 into left atrium 224.

As shown in FIG. 9G, a distal end 251 of sleeve 226 is positioned in a vicinity of a left fibrous trigone 242 of an annulus 243 of mitral valve 230. (It is noted that for clarity of illustration, distal end 251 of sleeve 226 is shown schematically in the cross-sectional view of the heart, although left trigone 242 is in reality not located in the shown cross-sectional plane, but rather out of the page closer to the viewer.) Alternatively, the tip is positioned in a vicinity of a right fibrous trigone 244 of the mitral valve (configuration not shown). Further alternatively, the distal tip of the sleeve is not positioned in the vicinity of either of the trigones, but is instead positioned elsewhere in a vicinity of the mitral valve, such as in a vicinity of the anterior or posterior commissure. The steering functionality of anchor manipulation area 50 typically allows the area near the distal end of the deployment tool to be positioned with six degrees of freedom. Once positioned at the desired site near the selected trigone, deployment tool 30 deploys a first anchor 32 through the wall of sleeve 226 into cardiac tissue near the trigone, using the techniques described hereinabove with reference to FIGS. 4A-C.

Figure 9H:
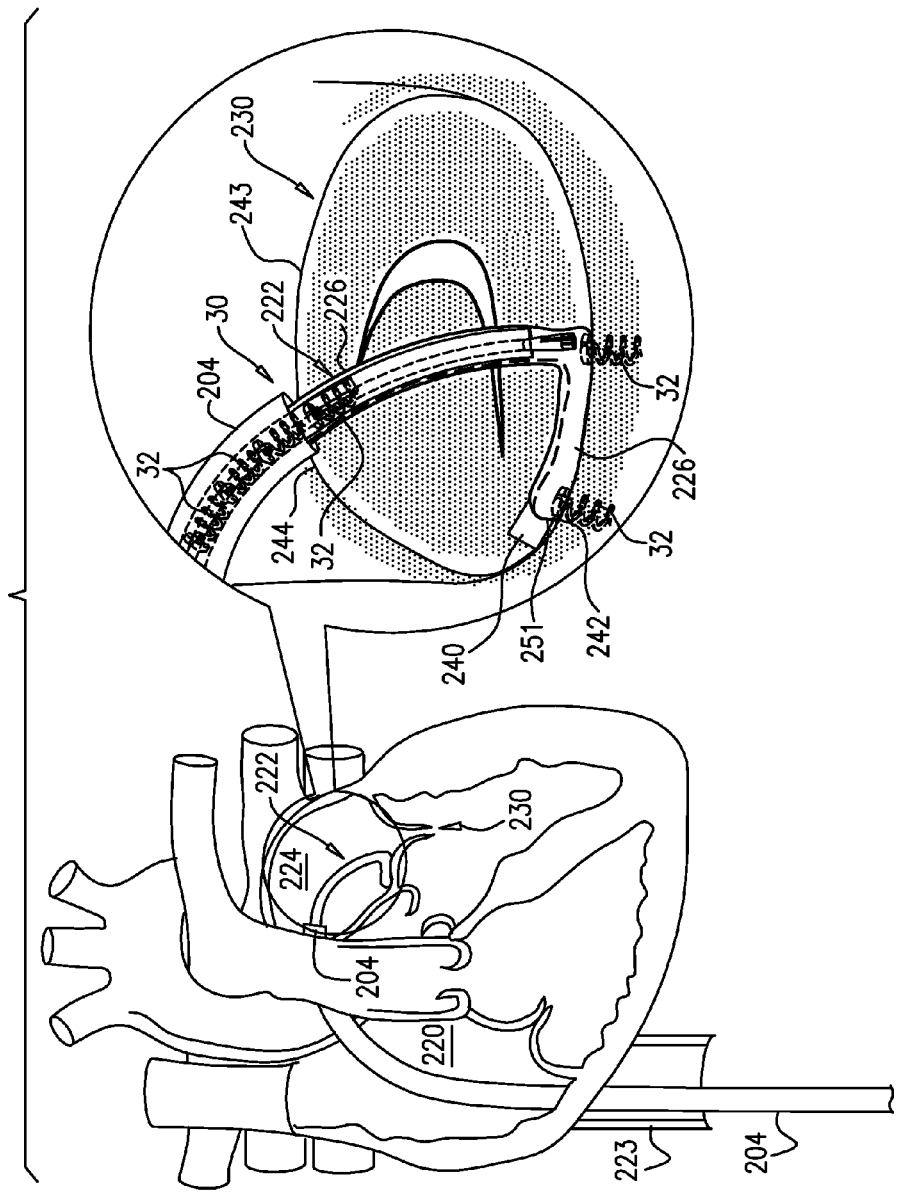

As shown in FIG. 9H, deployment tool 30 is repositioned along annulus 243 to another site selected for deployment of a second anchor 32. Typically, the first anchor is deployed most distally in the sleeve (generally at or within a few millimeters of the distal tip of the sleeve), and each subsequent anchor is deployed more proximally, such that the sleeve is gradually pulled off (i.e., withdrawn from) the deployment tool in a distal direction during the anchoring procedure. The already-deployed first anchor 32 holds the anchored end of sleeve 226 in place, so that the sleeve is drawn from the site of the first anchor towards the site of the second anchor. Typically, as the sleeve is pulled off (i.e., withdrawn from) the deployment tool, the deployment tool is moved generally laterally along the cardiac tissue, as shown in FIG. 9H.

Deployment tool 30 deploys the second anchor through the wall of the sleeve into cardiac tissue at the second site. Depending on the tension applied between the first and second anchor sites, the portion of sleeve 226 therebetween may remain tubular in shape, or may become flattened, which may help reduce any interference of the ring with blood flow.

The techniques described hereinabove with reference to FIG. 4D, followed again by those described with reference to FIGS. 4A-C, are used to provide and deploy the second and subsequent anchors one at a time at the selected sites, respectively.

Figure 9I:
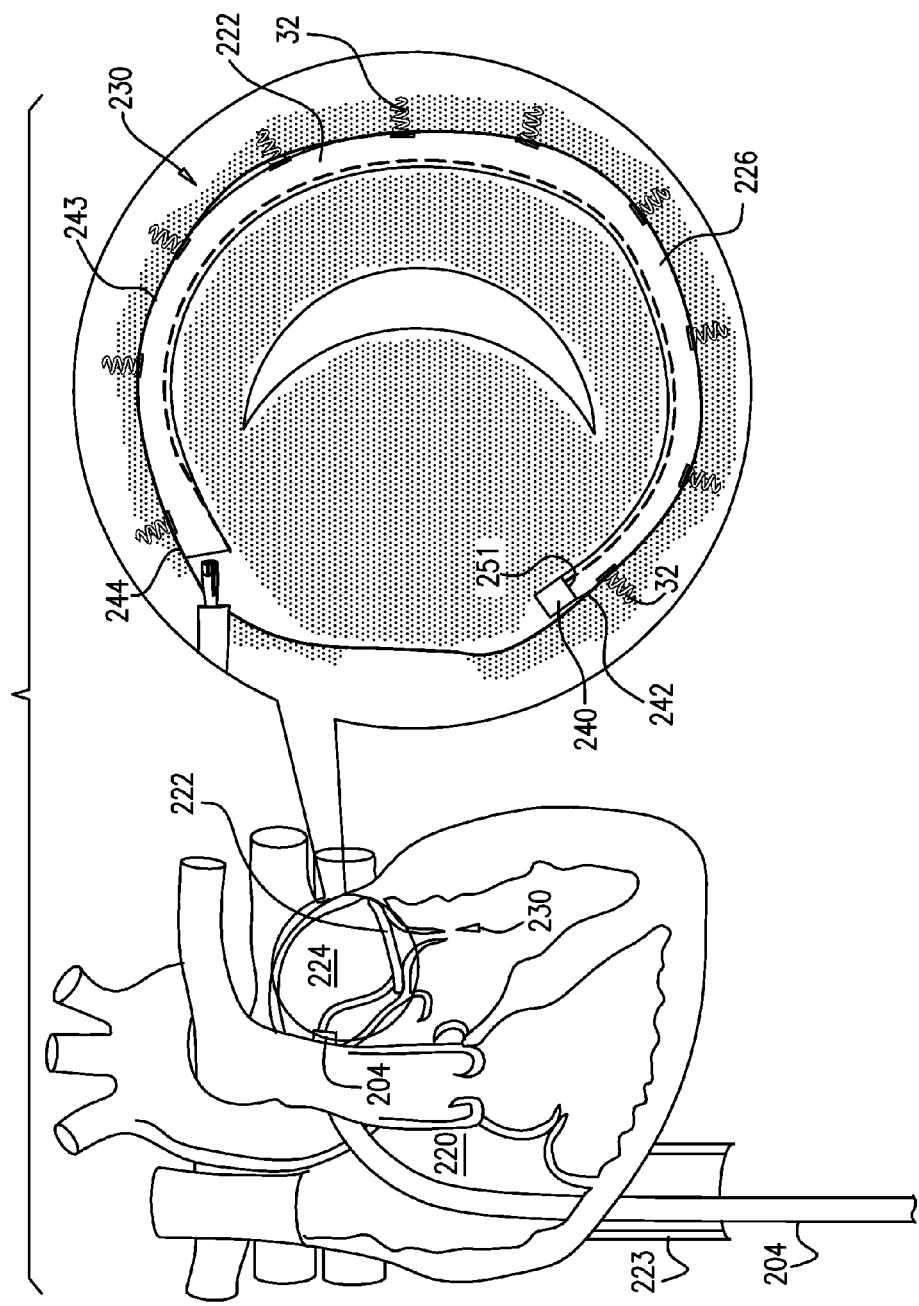

As shown in FIG. 9I, deployment tool 30 is repositioned along the annulus to additional sites, at which respective anchors are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. A rotation tool or anchor driver is used to rotate the spool of contracting mechanism 240, in order to tighten ring 222.

Alternatively, annuloplasty ring 222 is implanted by right or left thoracotomy, mutatis mutandis.

For some applications of the present invention, annuloplasty ring 222 is used to treat an atrioventricular valve other than the mitral valve, i.e., the tricuspid valve. For these applications, ring 222 and other components of system 20 described hereinabove as being placed in the left atrium are instead placed in the right atrium. Although annuloplasty ring 222 is described hereinabove as being placed in an atrium, for some application the ring is instead placed in either the left or right ventricle.

In an application of the present invention, anchor deployment system 20 is used in combination with mitral valve repair system 400, described with reference to FIGS. 17A-F, 18A-B, 19A-E, and 20A-B of International Application PCT/IL2009/000593, filed Jun. 15, 2009, which published as PCT Publication WO 10/004,546, and which is incorporated herein by reference. Instead of passing anchors through the lumen of the catheter from a site outside the body of the patient, as described with reference to FIG. 20B, the anchors are stored in anchor storage area 40 of anchor deployment tool 30.

For some applications, techniques described herein are practiced in combination with techniques described in one or more of the references cited in the Background section of the present patent application.

Additionally, the scope of the present invention includes embodiments described in the following applications, which are incorporated herein by reference. In an embodiment, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed Feb. 16, 2007;

U.S. Provisional Patent Application 61/001,013 to Gross et al., entitled, "Segmented ring placement," filed Oct. 29, 2007;

PCT Patent Application PCT/IL07/001,503 to Gross et al., entitled, "Segmented ring placement," filed Dec. 5, 2007, which published as WO 08/068,756;

U.S. patent application Ser. No. 11/950,930 to Gross et al., entitled, "Segmented ring placement," filed Dec. 5, 2007, which published as US Patent Application Publication 2008/0262609;

U.S. Provisional Patent Application 61/132,295 to Gross et al., entitled, "Annuloplasty devices and methods of delivery therefor," filed Jun. 16, 2008;

U.S. patent application Ser. No. 12/341,960 to Cabiri, entitled, "Adjustable partial annuloplasty ring and mechanism therefor," filed Dec. 22, 2008, which published as US 2010/0161047;

U.S. Provisional Patent Application 61/207,908 to Miller et al., entitled, "Actively-engageable movement-restriction mechanism for use with an annuloplasty structure," filed Feb. 17, 2009;

U.S. patent application Ser. No. 12/435,291 to Maisano et al., entitled, "Adjustable repair chords and spool mechanism therefor," filed May 4, 2009, which published as US 2010/0161041;

U.S. patent application Ser. No. 12/437,103 to Zipory et al., entitled, "Annuloplasty ring with intra-ring anchoring," filed May 7, 2009, which published as US 2010/0286767;

PCT Patent Application PCT/IL2009/000593 to Gross et al., entitled, "Annuloplasty devices and methods of delivery therefor," filed Jun. 15, 2009, which published as PCT Publication WO 10/004,546;

U.S. patent application Ser. No. 12/548,991 to Maisano et al., entitled, "Implantation of repair chords in the heart," filed Aug. 27, 2009, which published as US 2010/0161042;

U.S. patent application Ser. No. 12/608,316 to Miller et al., entitled, "Tissue anchor for annuloplasty ring," filed Oct. 29, 2009, which published as US 2011/0106247;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed Dec. 22, 2009, which published as WO 10/073,246;

U.S. patent application Ser. No. 12/689,635 to Zipory et al., entitled, "Over-wire rotation tool," filed Jan. 19, 2010, which published as US 2010/0280604;

U.S. patent application Ser. No. 12/689,693 to Hammer et al., entitled, "Deployment techniques for annuloplasty ring," filed Jan. 19, 2010, which published as US 2010/0280605;

U.S. patent application Ser. No. 12/706,868 to Miller et al., entitled, "Actively-engageable movement-restriction mechanism for use with an annuloplasty structure," filed Feb. 17, 2010, which published as US 2010/0211166;

PCT Patent Application PCT/IL2010/000357 to Maisano et al., entitled, "Implantation of repair chords in the heart," filed May 4, 2010, which published as WO 10/128,502;

PCT Patent Application PCT/IL2010/000358 to Zipory et al., entitled, "Deployment techniques for annuloplasty ring and over-wire rotation tool," filed May 4, 2010, which published as WO 10/128,503; and/or U.S. Regular application Ser. No. 12/785,717 to Miller et al., entitled, "Adjustable artificial chordeae tendineae with suture loops," filed May 24, 2010, which published as US 2011/0288635.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a plurality of tissue anchors; and
   an anchor deployment tool, which comprises:
   a flexible outer tube, which has a distal tube end, and which defines (a) an anchor storage area in which the plurality of tissue anchors are stored before deployment thereof, and (b) a flexible distal anchor manipulation area between the anchor storage area and the distal tube end, the anchor manipulation area having a length of at least 3 cm;
   a rotating deployment element, which is positioned within the flexible outer tube, and which is configured to:
      pass through one or more of the anchors without engaging the anchors when the rotating deployment element is withdrawn in a proximal direction within the outer tube,
      directly engage the anchors in the anchor storage area, a single one at a time, when the rotating deployment element is advanced in the distal direction against the one of the anchors,
      advance each of the anchors, while thus directly engaged, in a distal direction, and
      deploy each of the anchors through the distal tube end and into tissue of a subject by screwing the anchor into the tissue,
   wherein the anchor deployment tool is configured such that only the single anchor being advanced at the time by the rotating deployment element is within the distal anchor manipulation area.

2. The apparatus according to claim 1, wherein the rotating deployment element comprises a locking mechanism that is configured to selectively assume (a) a locked state, in which the locking mechanism, even upon withdrawal of the rotating deployment element in the proximal direction, prevents disengagement of the rotating deployment element from one of the anchors which the rotating deployment element engages, and (b) an unlocked state, in which the locking mechanism does not prevent disengagement of the rotating deployment element from the anchor upon the withdrawal of the rotating deployment element in the proximal direction.

3. The apparatus according to claim 1, wherein the distal anchor manipulation area comprises steering functionality.

4. The apparatus according to claim 1, wherein the length of the anchor storage area is at least 5 cm.

5. The apparatus according to claim 1, wherein the anchor storage area is configured to provide a plurality of anchor storage locations, wherein the anchors are initially stored in respective ones of at least a portion of the anchor storage locations, and wherein, when the rotating deployment element advances a distal-most one of the anchors out of the anchor storage area in the distal direction, the anchors remaining in the anchor storage area remain in their respective initial anchor storage locations.

6. The apparatus according to claim 1, wherein the plurality of anchors comprises at least 6 anchors.

7. The apparatus according to claim 1, wherein the anchor deployment tool further comprises an anchor restraining mechanism in a vicinity of a distal end of the anchor storage area, which mechanism is configured to temporarily restrain at least a distal-most one of the anchors currently stored in the anchor storage area from advancing in the distal direction.

8. The apparatus according to claim 1, further comprising an annuloplasty ring, which comprises a sleeve having a lumen, wherein the anchor deployment tool is configured to be removably positioned within the lumen of the sleeve, and, while so positioned, to deploy the anchors from the distal tube end through a wall of the sleeve into the tissue.

9. A method comprising:
   providing a plurality of tissue anchors;
   providing an anchor deployment tool, which includes (i) a flexible outer tube, which has a distal tube end, and which defines (a) an anchor storage area in which the plurality of tissue anchors are stored before deployment thereof, and (b) a flexible distal anchor manipulation area between the anchor storage area and the distal tube end, the anchor manipulation area having a length of at least 3 cm, and (ii) a rotating deployment element, which is positioned within the flexible outer tube;
   withdrawing the rotating deployment element in a proximal direction within the outer tube, such that the rotating deployment element passes through one or more of the anchors without engaging the anchors; and
   using the rotating deployment element, (a) directly engaging the anchors in the anchor storage area, a single one at a time, when the rotating deployment element is advanced in the distal direction against the one of the anchors, (b) advancing each of the anchors, while thus directly engaged, in a distal direction, such that only the single anchor being advanced at the time by the rotating deployment element is within the distal anchor manipulation area, and (c) deploying each of the anchors through the distal tube end and into tissue of a subject by screwing the anchor into the tissue.

10. The method according to claim 9,
   wherein the rotating deployment element includes a locking mechanism that is configured to selectively to assume a locked state, in which the locking mechanism, even upon withdrawal of the rotating deployment element in the proximal direction, prevents disengagement of the rotating deployment element from the anchor,
   wherein the method further comprises causing the locking mechanism to assume the locked state, and
   wherein withdrawing the anchor comprises withdrawing the anchor in the proximal direction while the rotating deployment element is in the locked state.

11. Apparatus comprising:
   a plurality of tissue anchors; and
   an anchor deployment tool, which (a) defines an anchor storage area in which the plurality of tissue anchors are stored before deployment thereof, and (b) comprises:
   a flexible outer tube, which has a distal tube end; and
   a rotating deployment element, which is positioned within the flexible outer tube, and which is configured to:
      pass through one or more of the anchors without engaging the anchors when the rotating deployment element is withdrawn in a proximal direction within the outer tube,
      directly engage the anchors in the anchor storage area, a single one at a time, when the rotating deployment element is advanced in the distal direction against the one of the anchors,
      advance each of the anchors, while thus directly engaged, in a distal direction, and
      deploy each of the anchors through the distal tube end and into tissue of a subject by rotating only the anchor directly engaged by the rotating deployment element, without rotating the anchors stored in the anchor storage area.

12. The apparatus according to claim 11, wherein the anchor storage area is configured to provide a plurality of anchor storage locations, wherein the anchors are initially stored in respective ones of at least a portion of the anchor storage locations, and wherein, when the rotating deployment element advances a distal-most one of the anchors out of the anchor storage area in the distal direction, the anchors remaining in the anchor storage area remain in their respective initial anchor storage locations.

13. The apparatus according to claim 11, wherein the plurality of anchors comprises at least 6 anchors.

14. The apparatus according to claim 11, wherein the anchor deployment tool further comprises an anchor restraining mechanism in a vicinity of a distal end of the anchor storage area, which mechanism is configured to temporarily restrain at least a distal-most one of the anchors currently stored in the anchor storage area from advancing in the distal direction.

15. Apparatus comprising:
a plurality of tissue anchors, which are shaped so as to define respective channels along entire longitudinal lengths of the anchors; and
an anchor deployment tool, which (a) defines an anchor storage area and (b) comprises:
a flexible outer tube, which has a distal tube end;
a flexible inner shaft, which is positioned within the flexible outer tube; and
a rotating deployment element, which is positioned within the flexible outer tube and is coupled to a distal shaft end of the flexible inner shaft, and which is configured to:
directly engage the anchors in the anchor storage area, a single one at a time,
advance each of the anchors, while thus directly engaged, in a distal direction, and
deploy each of the anchors through the distal tube end and into tissue of a subject by screwing the anchor into the tissue,
wherein the plurality of tissue anchors are stored in the anchor storage area before deployment thereof, such that the flexible inner shaft passes through the channels of the stored anchors without engaging the stored anchors, and the stored anchors are within the flexible outer tube.

16. The apparatus according to claim 15, wherein the rotating deployment element directly engages the anchors in the anchor storage area, a single one at a time.

17. The apparatus according to claim 16, wherein the rotating deployment element advances each of the anchors, while thus directly engaged, in the distal direction.

18. The apparatus according to claim 17, wherein the rotating deployment element deploys each of the anchors through the distal end and into the tissue of the subject by screwing the anchor into the tissue.

19. The apparatus according to claim 15, wherein the rotating deployment element is configured to pass through one or more of the anchors without engaging the anchors when the rotating deployment element is withdrawn in a proximal direction within the outer tube, and to directly engage one of the anchors when the rotating deployment element is advanced in the distal direction against the one of the anchors.

20. The apparatus according to claim 15, wherein the anchor storage area is configured to provide a plurality of anchor storage locations, wherein the anchors are initially stored in respective ones of at least a portion of the anchor storage locations, and wherein, when the rotating deployment element advances a distal-most one of the anchors out of the anchor storage area in the distal direction, the anchors remaining in the anchor storage area remain in their respective initial anchor storage locations.

21. The apparatus according to claim 15, wherein the plurality of anchors comprises at least 6 anchors.

22. The apparatus according to claim 15, wherein the anchor deployment tool further comprises an anchor restraining mechanism in a vicinity of a distal end of the anchor storage area, which mechanism is configured to temporarily restrain at least a distal-most one of the anchors currently stored in the anchor storage area from advancing in the distal direction.

23. A method comprising:
providing a plurality of tissue anchors;
providing an anchor deployment tool, which (a) defines an anchor storage area in which the plurality of tissue anchors are stored before deployment thereof, and (b) includes (i) a flexible outer tube, which has a distal tube end, and (ii) a rotating deployment element, which is positioned within the flexible outer tube;
withdrawing the rotating deployment element in a proximal direction within the outer tube, such that the rotating deployment element passes through one or more of the anchors without engaging the anchors; and
using the rotating deployment element, (a) directly engaging the anchors in the anchor storage area, a single one at a time, when the rotating deployment element is advanced in the distal direction against the one of the anchors, (b) advancing each of the anchors, while thus directly engaged, in a distal direction, and (c) deploying each of the anchors through the distal tube end and into tissue of a subject by rotating only the anchor directly engaged by the rotating deployment element, without rotating the anchors stored in the anchor storage area.

24. A method comprising:
providing a plurality of tissue anchors, which are shaped so as to define respective channels along entire longitudinal lengths of the anchors;
providing an anchor deployment tool, which (a) defines an anchor storage area and (b) includes (i) a flexible outer tube, which has a distal tube end, (ii) a flexible inner shaft, which is positioned within the flexible outer tube, and (iii) a rotating deployment element, which is positioned within the flexible outer tube and is coupled to a distal shaft end of the flexible inner shaft; and
using the rotating deployment element, (a) directly engaging the anchors in the anchor storage area, a single one at a time, (b) advancing each of the anchors, while thus directly engaged, in a distal direction, and (c) deploying each of the anchors through the distal tube end and into tissue of a subject by screwing the anchor into the tissue,
wherein the plurality of tissue anchors are stored in the anchor storage area before deployment thereof, such that the flexible inner shaft passes through the channels of the stored anchors without engaging the stored anchors, and the stored anchors are within the flexible outer tube.

* * * * *